US012599725B2

(12) United States Patent
Wallace et al.

(10) Patent No.: US 12,599,725 B2
(45) Date of Patent: Apr. 14, 2026

(54) DRIVE MECHANISM FOR AN INJECTION DEVICE

(71) Applicant: SANOFI, Paris (FR)

(72) Inventors: Andrew Gordon Wallace, Warwick (GB); Andrew Mark Lindsay, Warwick (GB); Georgina Millington, Warwick (GB); Matthew Meredith Jones, Warwick (GB); William Geoffrey Arthur Marsh, Warwick (GB); Anthony Paul Morris, Warwick (GB)

(73) Assignee: Sanofi, Paris (FR)

( * ) Notice: Subject to any disclaimer, the term of this patent is extended or adjusted under 35 U.S.C. 154(b) by 1575 days.

(21) Appl. No.: 16/981,619

(22) PCT Filed: Mar. 15, 2019

(86) PCT No.: PCT/EP2019/056522
§ 371 (c)(1),
(2) Date: Sep. 16, 2020

(87) PCT Pub. No.: WO2019/179885
PCT Pub. Date: Sep. 26, 2019

(65) Prior Publication Data
US 2021/0016013 A1 Jan. 21, 2021

(30) Foreign Application Priority Data
Mar. 19, 2018 (EP) ..................................... 18305303

(51) Int. Cl.
*A61M 5/315* (2006.01)
*A61M 5/20* (2006.01)
(Continued)

(52) U.S. Cl.
CPC ...... *A61M 5/31536* (2013.01); *A61M 5/2033* (2013.01); *A61M 5/281* (2013.01);
(Continued)

(58) Field of Classification Search
CPC ............ A61M 5/31553; A61M 5/3155; A61M 5/31571
See application file for complete search history.

(56) References Cited

U.S. PATENT DOCUMENTS 5,591,136 A * 1/1997 Gabriel ............. A61M 5/31553
604/211
7,195,616 B2 * 3/2007 Diller ....................... G01D 5/25
604/207
(Continued)

FOREIGN PATENT DOCUMENTS

EP 2258425 A2 † 12/2010
EP 2776092 B1 † 3/2016
(Continued)

OTHER PUBLICATIONS

PCT International Preliminary Report on Patentability in International Appln. No. PCT/EP2019/056522, dated Sep. 22, 2020, 8 pages.
(Continued)

*Primary Examiner* — Bhisma Mehta
*Assistant Examiner* — Adam J. Cermak
(74) *Attorney, Agent, or Firm* — Fish & Richardson P.C.

(57) ABSTRACT

An injection device for expelling a number of preset or user-selectable doses of a medicament. The injection device includes: an elongated housing extending along a longitudinal axis, and a rotatable member and a counterpart member each comprising a first mechanical code and a second mechanical code, respectively. For setting a dose, the rotatable member is rotatable relative to the housing and relative
(Continued)

to the counterpart member. During the setting of the dose, the rotatable member is constrained along the longitudinal axis relative to the housing or relative to the counterpart member. For expelling a dose, one of the rotatable member and the counterpart member is displaceable along the longitudinal axis into an expelling position relative to the other one of the rotatable member and the counterpart member only when the first mechanical code is aligned with the second mechanical code.

18 Claims, 15 Drawing Sheets

(51) Int. Cl.
   *A61M 5/28*      (2006.01)
   *A61M 5/31*      (2006.01)

(52) U.S. Cl.
   CPC .... *A61M 5/31551* (2013.01); *A61M 5/31585* (2013.01); *A61M 2005/3126* (2013.01)

(56)                References Cited

U.S. PATENT DOCUMENTS

| | | | | |
|---|---|---|---|---|
| 10,744,270 | B2 | 8/2020 | Avery et al. | |
| 2005/0177116 | A1* | 8/2005 | Graf ................. | A61M 5/31553 604/208 |
| 2007/0167921 | A1* | 7/2007 | Burren ............... | A61M 5/3158 604/211 |
| 2009/0227955 | A1* | 9/2009 | Hirschel .......... | A61M 5/31583 604/187 |
| 2013/0245561 | A1* | 9/2013 | Kouyoumjian ..... | A61M 5/3294 604/191 |
| 2014/0228769 | A1* | 8/2014 | Karlsson .......... | A61M 5/31553 604/197 |
| 2014/0257195 | A1* | 9/2014 | Kjeldsen .......... | A61M 5/31541 604/207 |
| 2014/0350481 | A1* | 11/2014 | Raab ................ | A61M 5/31501 604/211 |
| 2015/0080811 | A1* | 3/2015 | Wieselblad ....... | A61M 5/31576 604/207 |
| 2015/0112274 | A1* | 4/2015 | Quinn ............... | A61M 5/31585 604/207 |
| 2015/0352287 | A1* | 12/2015 | Mercer ............ | A61M 5/31551 604/207 |
| 2015/0352290 | A1* | 12/2015 | Steel ................ | A61M 5/31528 604/211 |
| 2016/0082195 | A1* | 3/2016 | Atterbury ............... | G01D 5/25 |
| 2016/0151581 | A1* | 6/2016 | Giambattista ..... | A61M 5/31536 604/211 |
| 2016/0193417 | A1* | 7/2016 | Guillermo .......... | A61M 5/3202 604/224 |
| 2017/0354785 | A1* | 12/2017 | Gazeley ............. | A61M 5/3293 |
| 2018/0369491 | A1* | 12/2018 | Gaillot ............... | A61M 5/3158 |
| 2019/0015595 | A1* | 1/2019 | Keitel ................ | A61M 5/3146 |
| 2019/0224413 | A1* | 7/2019 | Hewson ........... | A61M 5/31553 |
| 2019/0374721 | A1* | 12/2019 | Smith ............... | A61M 5/31535 |
| 2020/0289762 | A1* | 9/2020 | Keitel .............. | A61M 5/31541 |
| 2021/0330891 | A1* | 10/2021 | Byerly ................... | A61M 5/20 |

FOREIGN PATENT DOCUMENTS

| | | | | |
|---|---|---|---|---|
| EP | 3106192 | A1 † | 12/2016 | |
| EP | 3181170 | | 6/2017 | |
| EP | 3181170 | A1 * | 6/2017 | ........ A61M 5/31583 |
| EP | 2244768 | B1 † | 4/2019 | |
| JP | 2006-507035 | | 3/2006 | |
| JP | 2012528642 | A * | 11/2012 | ........ A61M 5/31586 |
| JP | 2017-520370 | | 7/2017 | |
| JP | 2017-534364 | A | 11/2017 | |
| WO | WO-2009092807 | A1 * | 7/2009 | .............. A61M 5/20 |
| WO | WO-2014033197 | A1 * | 3/2014 | ........ A61M 5/31541 |
| WO | WO 2016/001299 | | 1/2016 | |
| WO | WO 2016//055619 | A1 | 4/2016 | |
| WO | WO 2019/102027 | A1 | 5/2019 | |

OTHER PUBLICATIONS

PCT International Search Report and Written Opinion in International Appln. No. PCT/EP2019/056522, dated Apr. 23, 2019, 11 pages.

\* cited by examiner
† cited by third party

Figure 1
Figure 2
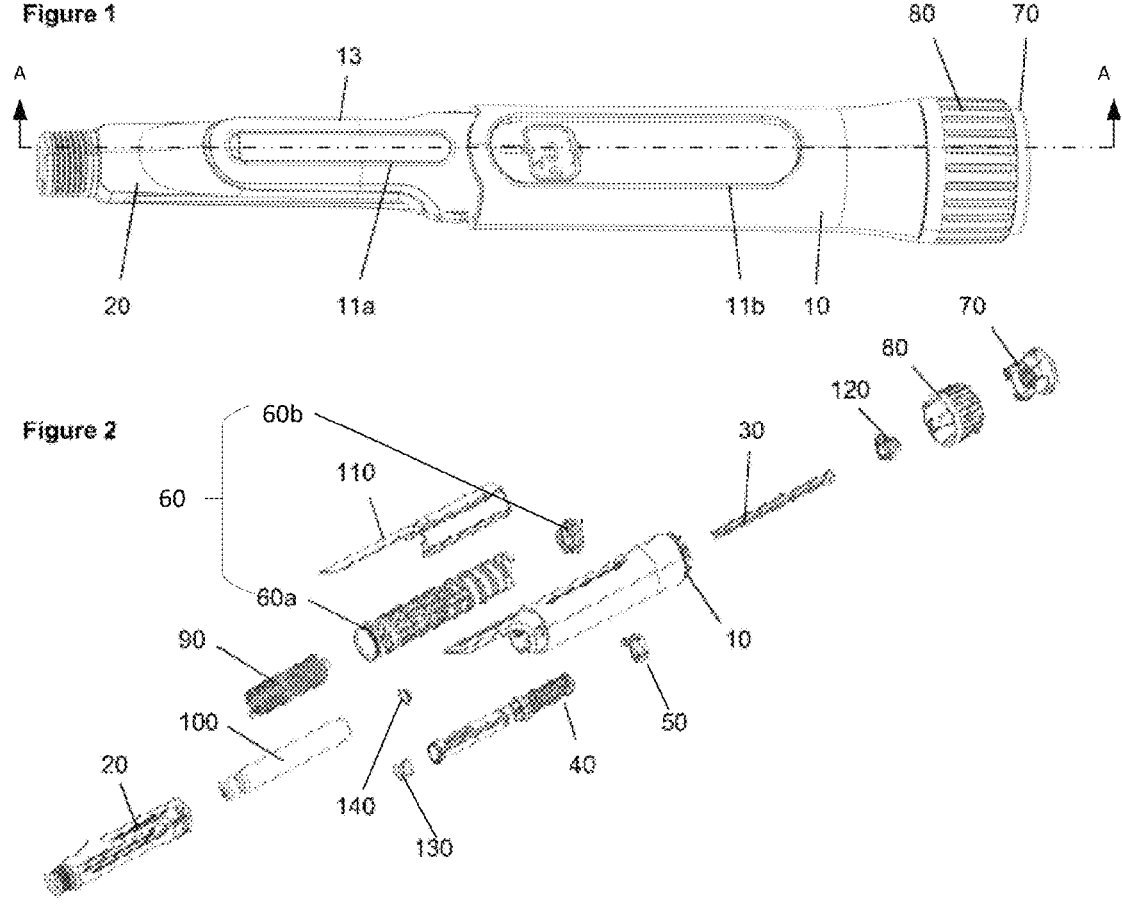
Figure 3
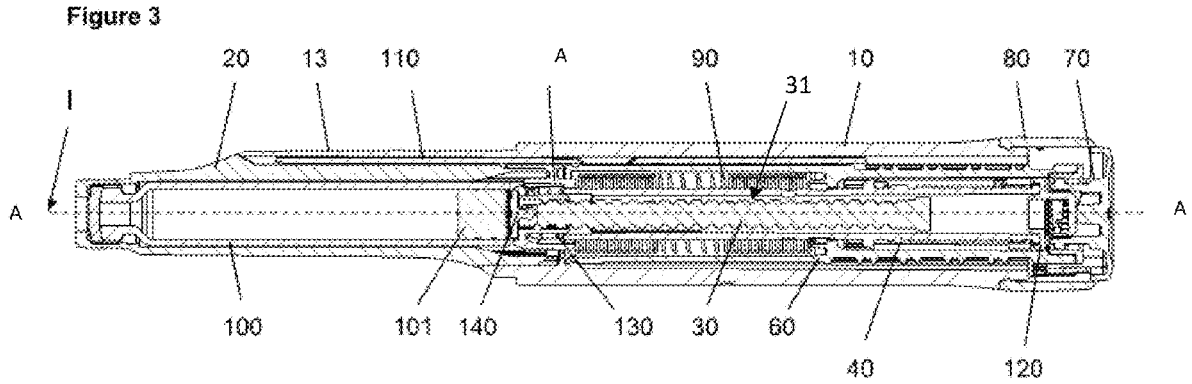

Figure 4a
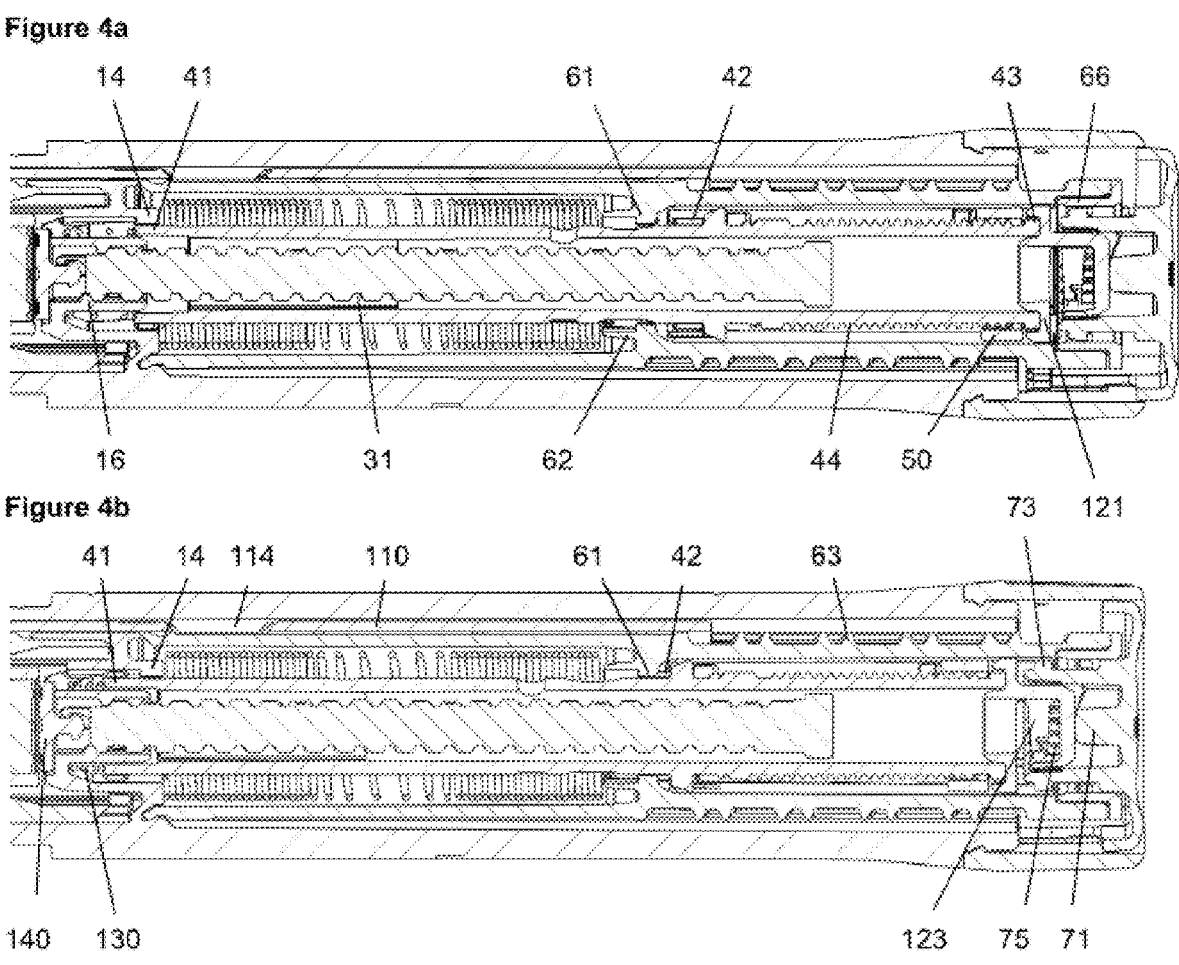
Figure 4b
Figure 5a
Figure 5b
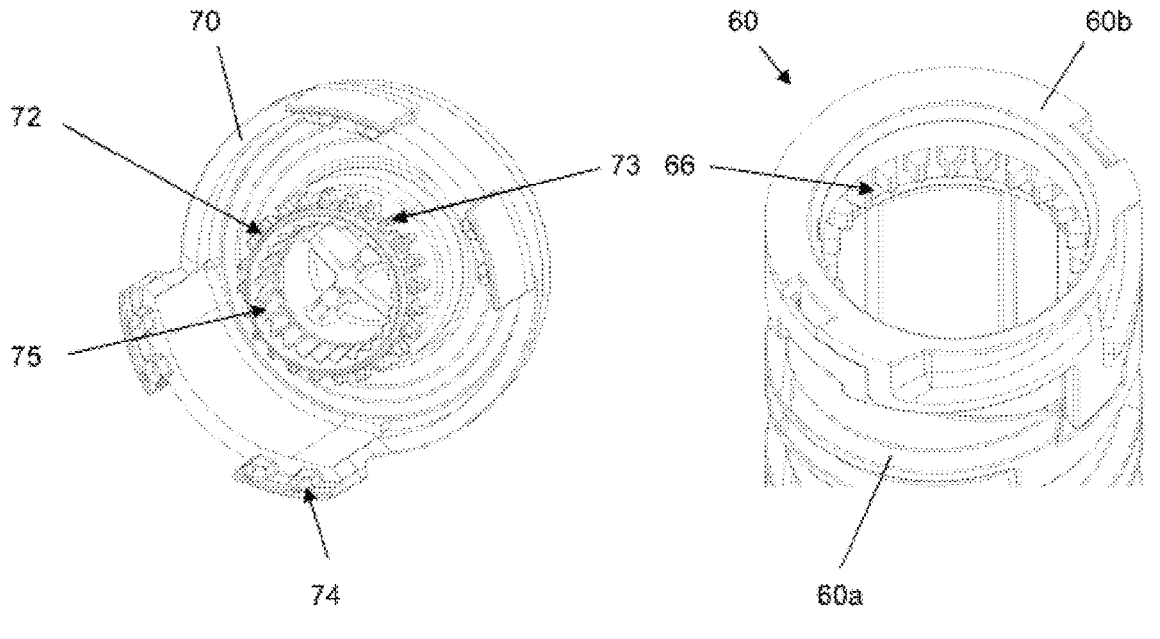

Figure 6
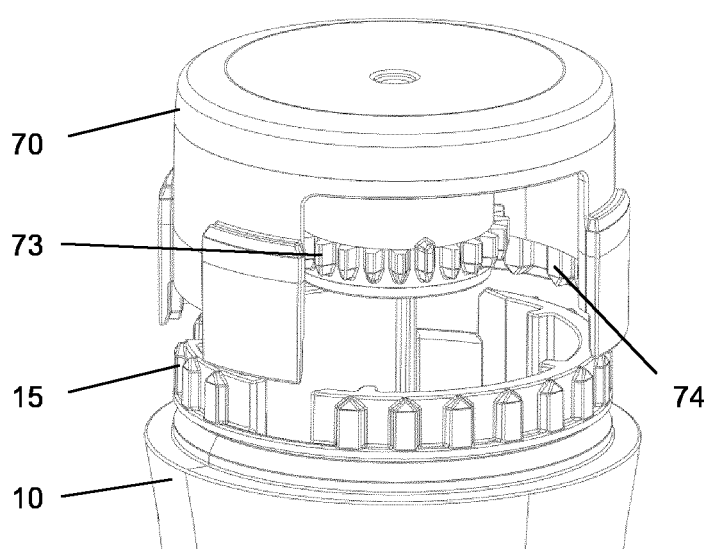
Figure 7a
Figure 7b
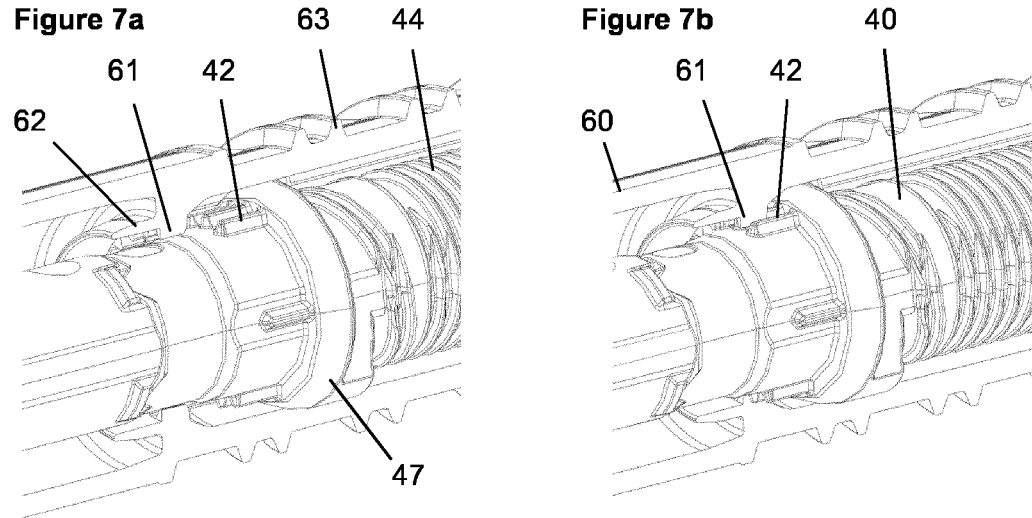
Figure 8
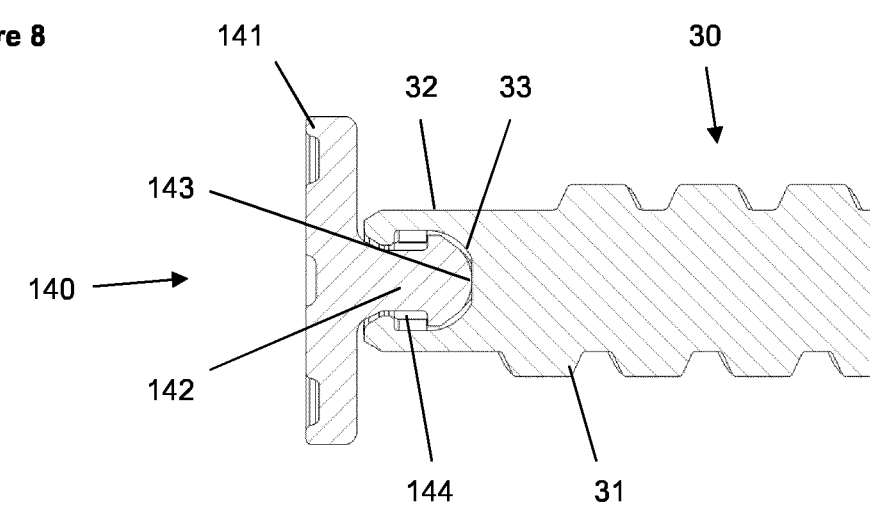

Figure 15
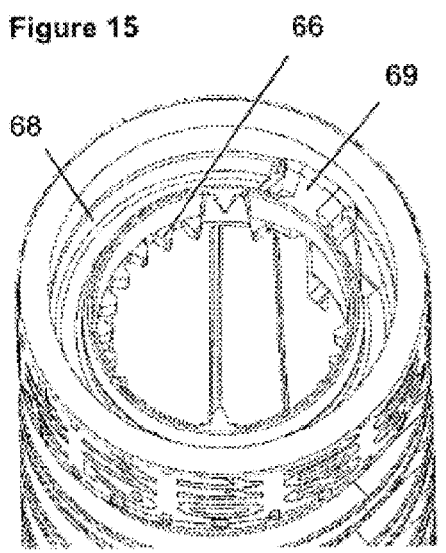
Figure 16
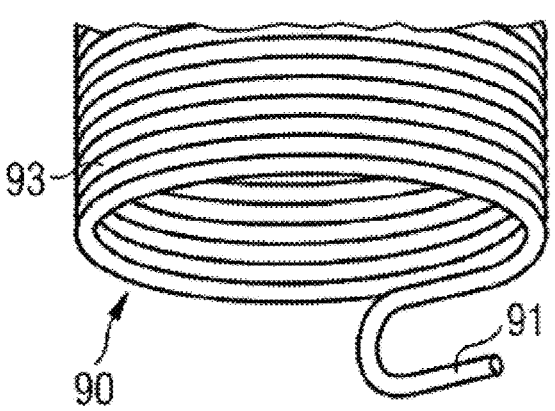
Figure 17a
Figure 17b
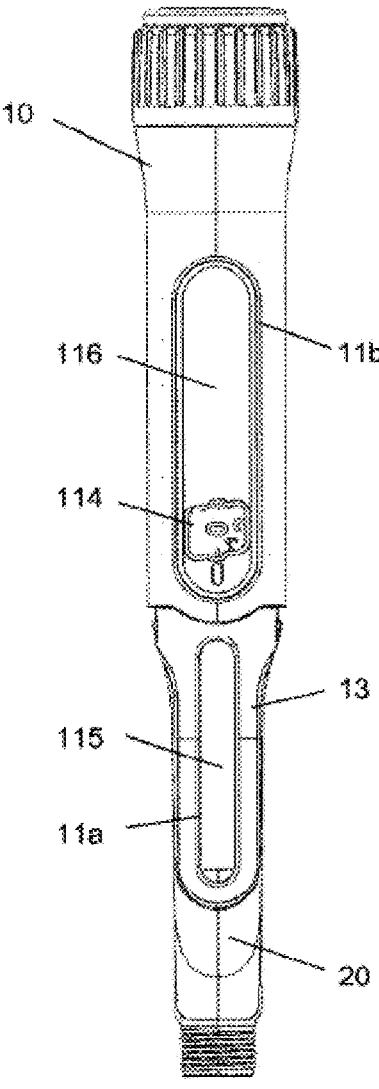
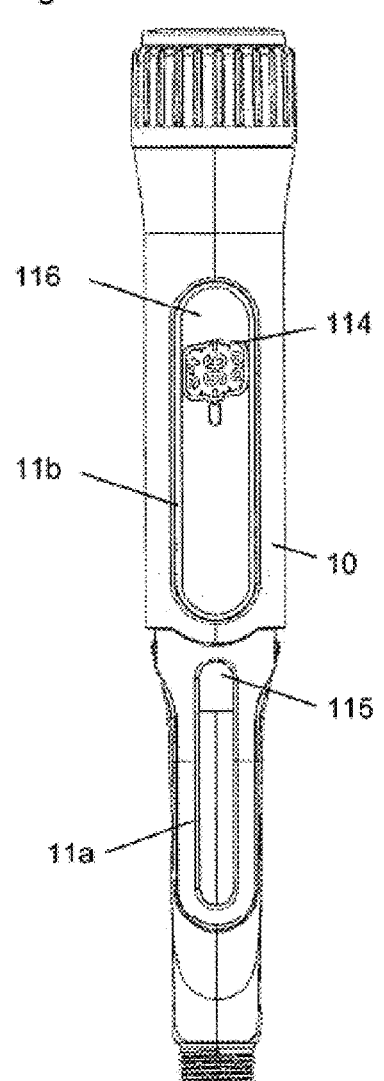

Figure 18
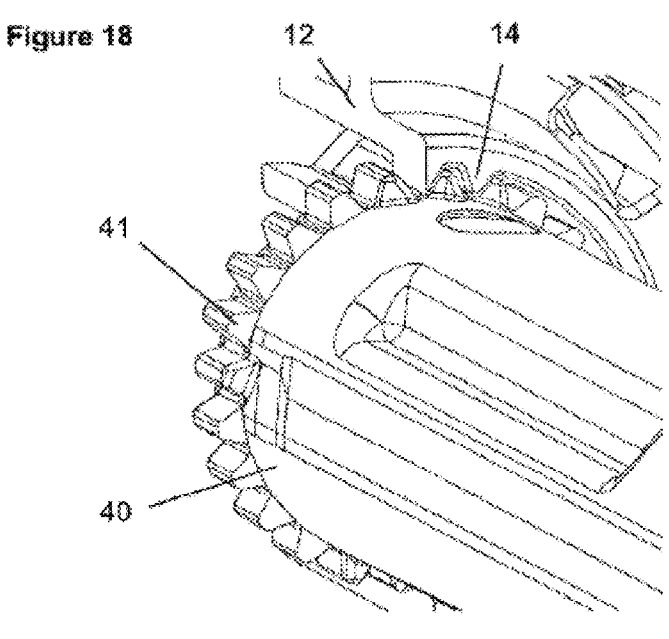
Figure 19a
Figure 19b
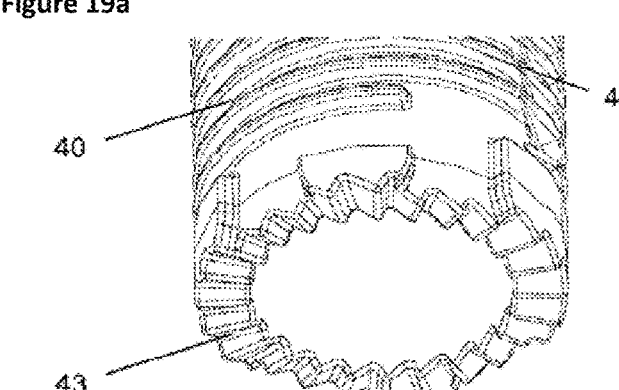
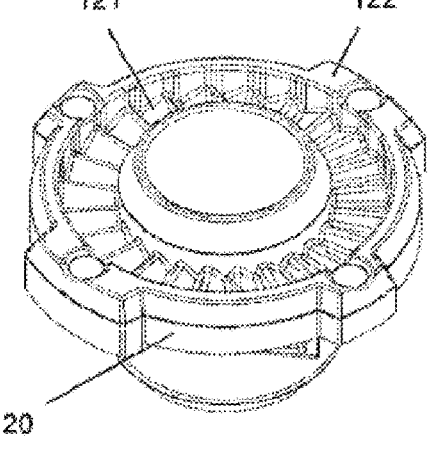
Figure 20
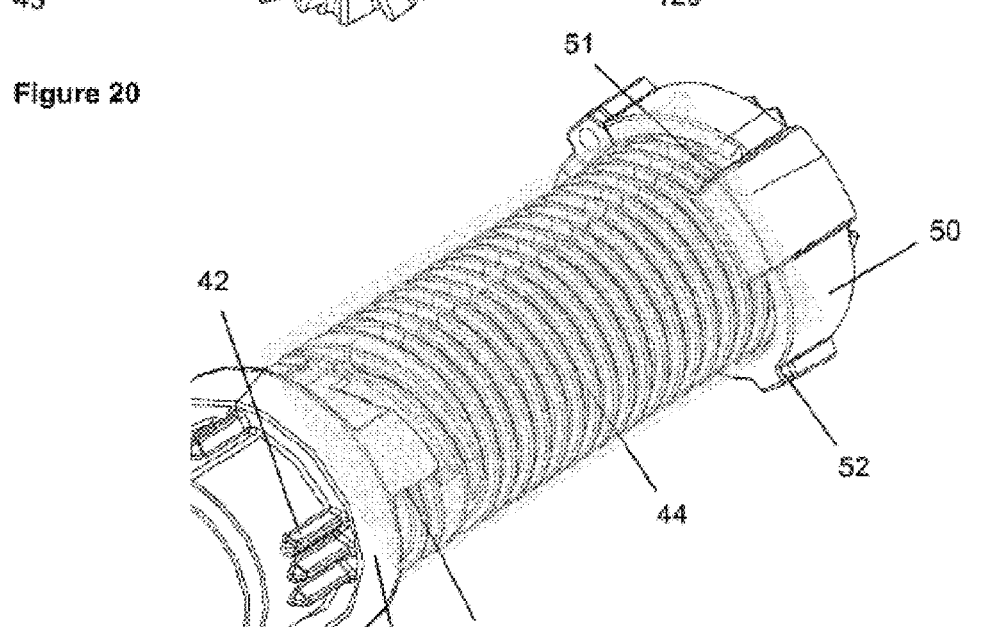

Figure 21
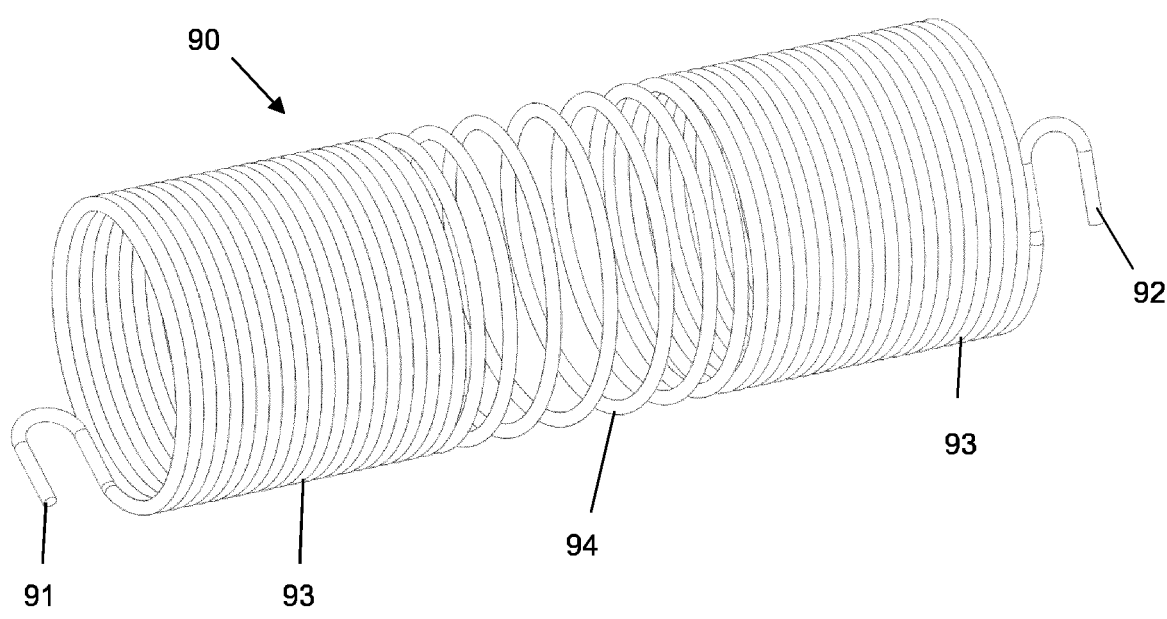
Figure 22a          Figure 22b          Figure 22c
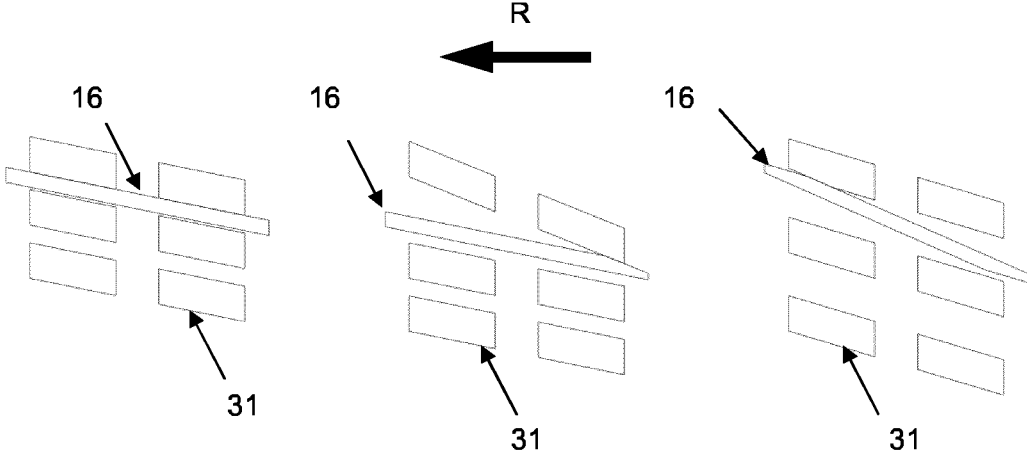

DRIVE MECHANISM FOR AN INJECTION DEVICE

CROSS-REFERENCE TO RELATED APPLICATIONS

The present application is the national stage entry of International Patent Application No. PCT/EP2019/056522, filed on Mar. 15, 2019, and claims priority to Application No. EP 18305303.2, filed on Mar. 19, 2018, the disclosures of which are incorporated herein by reference.

TECHNICAL FIELD

The present disclosure relates in one aspect to an injection device, like a pen-type injector for expelling of preset or user-selectable doses of a medicament. In particular, the disclosure relates to an injection device comprising an expelling mechanism, such as a windup expelling mechanism and comprising a dose setting mechanism, wherein the dose setting mechanism is configured to impede or to block a dose expelling procedure when the dose actually set does not match a predefined or prescribed dose size.

BACKGROUND

Injection devices for setting and dispensing a single or multiple doses of a liquid medicament are well-known in the art. Generally, such devices have a substantially similar purpose as that of an ordinary syringe.

Injection devices, in particular pen-type injectors have to meet a number of user-specific requirements. For instance, with patient's suffering chronic diseases, like diabetes, the patient may be physically infirm and may also have impaired vision. Suitable injection devices especially intended for home medication therefore need to be robust in construction and should be easy to use. Furthermore, manipulation and general handling of the device and its components should be intelligible and easily understandable. Moreover, a dose setting as well as a dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism or expelling mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

For some applications it can be advantageous to limit the minimum medicament dose that can be delivered from a device as well as the maximum dose. This may, for example, ensure that only a therapeutically effective dose can be administered. Such a functionality may be particularly relevant to combinations of drugs, where a minimum quantity of the combined drug is required to ensure sufficient delivery of one element of the combination to be therapeutically effective, whilst allowing some variation of the dose, which may be important for the other element of the combination.

For some applications it may be advantageous to offer a device which allows delivery of only one fixed dose value or a multiple thereof. It may be desirable to offer a device that allows delivery of a minimum fixed dose value and integer multiples of the minimum fixed dose value.

A further application could be for a therapy in which a range of discrete, non-sequential doses of a medication may be required. For example, a range of doses may be needed to satisfy the therapeutic needs of different user groups, or to allow individual users to deliver a different dose at different times of the day e.g., in the morning or in the evening.

It is therefore desirable to have an injection device that provides a limitation of deliverable dose values to a limited number of generally available dose values. The injection device should allow delivery of only one or several fixed dose values. The injection device should be configured to prevent setting or expelling of doses that do not match with a pre-described or predefined dose size.

SUMMARY

In one aspect an injection device is provided for expelling of a number of preset or user selectable doses of a medicament, typically of a liquid medicament. The injection device comprises an elongated housing extending along a longitudinal axis or along a principal axis. The housing is configured to accommodate a cartridge containing the medicament and having a bung sealing a proximal end of the cartridge. The injection device further comprises an expelling mechanism comprising a trigger and a piston rod. When induced by the trigger the piston rod is configured to urge against the bung along the longitudinal axis in a distal direction relative to the housing. The drive mechanism is configured to apply a driving force or a driving momentum to the piston rod by depressing the trigger in distal direction so as to urge the piston rod against the bung for expelling the medicament from a distal end of the cartridge.

The injection device further comprises a dose setting mechanism. The dose setting mechanism comprises a rotatable member and a counterpart member. The counterpart member comprises a first mechanical code/pattern (hereafter referred to as code). The rotatable member comprises a second mechanical code. The first and the second mechanical codes are complementary-shaped. The first mechanical code corresponds to the code of the second mechanical code and vice versa.

For setting of a dose the rotatable element is rotatable relative to the housing and relative to the counterpart member within a range of numerous rotational states. During setting of the dose the rotatable member is constrained along the longitudinal axis relative to the housing or relative to the counterpart member. In other words, at least during setting of the dose the rotatable member is exclusively subject to a rotational motion relative to the housing and/or relative to the counterpart member. At least during setting of a dose the rotatable member is axially constrained or axially fixed to the housing and/or to the counterpart member.

For expelling of a dose one of the rotatable member and the counterpart member is displaceable along the longitudinal axis into an expelling position relative to the other one of the rotatable member and the counterpart member only when the first mechanical code is aligned with the second mechanical code. If the first mechanical code is out of alignment to the second mechanical code a mutual relative longitudinal displacement of the rotatable member and the counterpart member to reach the expelling position is effectively blocked or impeded by the non-matching or mechanical codes of the rotatable member and the counterpart member.

By means of the mutually corresponding and complementary-shaped first and second mechanical codes of the rotatable member and the counterpart member a longitudinal or axial displacement of the rotatable member relative to the counterpart member is limited to such configurations of the rotatable member, wherein the first mechanical code is aligned to the second mechanical code.

Typically, the expelling mechanism and the dose setting mechanism are switchable between a dose expelling mode and a dose setting mode. In dose setting mode the piston rod is immobilized while a user is offered the possibility to set a dose of desired size. Dose setting may be accompanied by a rotation of the rotatable member. Generally, the rotatable member is rotatable relative to the counterpart member and relative to the housing within a range of numerous discrete rotational states. Each discrete rotational state may correspond to a standard unit of a dose of the medicament. When, during dose setting, the rotatable member is rotated from one discrete rotational state to a consecutive discrete rotational state the dose size may increase by a standard unit or by a multiple of a standard unit of the medicament.

The first and the second mechanical codes are configured and selected such that among the range of numerous rotational states only with a few predefined rotational states of the rotatable member the first mechanical code aligns with the second mechanical code thus enabling a relative axial or longitudinal displacement of the rotatable member relative to the counterpart member. In this way, the number of differently sized dose values that can be set and dispensed by the injection device can be reduced to a desired minimum. Typically, the first and second mechanical codes are configured to allow setting and dispensing of at least one predefined size of a dose. The first and second mechanical codes may be further configured to allow and to support setting and dispensing of a second predefined dose and/or of a third predefined dose. The second predefined dose may be twice as large as the first predefined dose. In particular, the first and the second mechanical codes may be configured to allow and support setting and dispensing of one predefined dose size and further dose sizes that are an integer multiple of the predefined dose size.

It may be of particular benefit that the rotatable member and/or the counterpart member is integrated into an existing component of an injection device. Implementation of the first mechanical code into the counterpart member and integration of the second mechanical code into the rotatable member may only require a redesign or restructuring of at least one of the counterpart member and the rotatable member that are present in the injection device anyway. Insofar, the functionality of the injection device as described herein can be generally obtained without the implementation of additional mechanical components to the dose setting mechanism or to the expelling mechanism.

The expelling mechanism may comprise a wind up expelling mechanism. Such a wind up expelling mechanism comprises inter alia a mechanical energy reservoir. The mechanical energy reservoir can be pre-loaded or pre-biased as the injection device is manufactured.

Optionally, the mechanical energy reservoir may be further biased or tensed as a dose is actually dialled or set through the dose setting mechanism. In this way, mechanical energy stored in the mechanical energy reservoir can be increased during dose setting.

Typically and during dose setting the mechanical energy reservoir is coupled to the piston rod in order to transfer a driving force or a driving torque to the piston rod for driving and displacing the same into the distal direction. Release of the energy from the mechanical energy reservoir to the piston rod may be controlled and/or triggered by the trigger. By means of one or several clutches the mechanical energy of the energy reservoir is transferrable into a driving momentum or driving force acting on the piston rod for driving the same in distal direction relative to the housing. The trigger may be operably connected to one or several clutches of the wind up expelling mechanism and/or of the dose setting mechanism in order to release a distally directed motion of the piston rod under the effect of a depleting mechanical energy reservoir.

The first mechanical code is complementary-shaped to the second mechanical code and vice versa. During setting of a dose and while the at least one of the rotatable member and the counterpart member is in a dose setting position the first mechanical code may be axially offset from the second mechanical code. The first mechanical code may be located at an axial or longitudinal distance from the second mechanical code as long as the dose setting mechanism and/or the expelling mechanism is in the dose setting mode.

The injection device is switchable into the dose expelling mode by displacing at least one of the rotatable member and the counterpart member into the expelling position. When the at least one of the rotatable member and the counterpart member is in the expelling position or arrives in the expelling position the injection device is switched into the dose dispensing mode. When in the dose dispensing mode the piston rod is subject to a distally directed advancing motion thus urging against the bung. Switching from the dose setting mode into the dose expelling mode is typically induced by depressing the trigger relative to the housing, typically in distal direction. The distally directed displacement of the trigger is transferred either directly or via at least one additional member, e.g., by a clutch onto one of the rotatable member and the counterpart member thus inducing a respective longitudinal displacement of the counterpart member relative to the rotatable member.

For switching the injection device into the dose expelling mode at least one of the rotatable member and the counterpart member is typically subject to a longitudinal or axial sliding displacement relative to the housing of the injection device. For instance, one of the rotatable member and the counterpart member is subject to a distally directed sliding displacement relative to the housing while the other one of the rotatable member and the counterpart member is axially fixed relative to the housing. For switching the injection device from the dose setting mode into the dose expelling mode one of the rotatable member and the counterpart member is axially displaceable, e.g., slidably axially displaceable relative to the other one of the rotatable member and the counterpart member.

If the first mechanical code and the second mechanical code are out of alignment the axial or longitudinal displacement of the rotatable member relative to the counterpart member is blocked by the first and second mechanical codes thus impeding and preventing a switching of the injection device into the dose expelling mode.

It is even conceivable, that the mechanical blocking inducible by the first and second mechanical codes out of alignment is transferred back to the trigger, which as long as the first and second mechanical codes are out of alignment cannot be fully depressed in distal direction. In this way, an immediate feedback is given to a user. As long as the first and second mechanical codes are out of alignment and hence as long as the dose actually set does not match a predefined dose size a dose expelling action of the injection device cannot be initiated or triggered. Eventually, the trigger of the expelling mechanism cannot be fully depressed in distal direction.

For switching of the injection device from the dose setting mode into the dose expelling mode at least one of the rotatable member and the counterpart member is displaceable relative to the other one of the rotatable member and the counterpart member. For instance, in one example the rotatable member may be axially constrained along the longitudinal axis relative to the housing only when the injection device is in the dose setting mode. For switching the injection device into the dose dispensing mode the rotatable member may be axially displaceable relative to the housing and relative to the counterpart member. Here, the counterpart member may be steadfastly attached to the housing. In another example it may be the counterpart member that is exclusively subject to a longitudinal displacement during switching of the device from the dose setting mode into the dose expelling mode. Here, the rotatable member may be axially fixed to the housing during dose setting as well as during dose expelling. In further examples it is even conceivable, that for switching of the injection device from the dose setting mode into the dose expelling mode both, the rotatable member and the counterpart member are subject to a longitudinal displacement relative to the housing and relative to each other.

According to a further example a longitudinal displacement of one of the rotatable member and the counterpart member into the expelling position is impeded as long as the first mechanical code and the second mechanical code are out of alignment. Only, when the first and the second mechanical codes are mutually aligned they allow and enable a longitudinal relative displacement thereof. When appropriately aligned the first mechanical code may receive at least a portion of the second mechanical code and vice versa. The first and the second mechanical codes are arrangeable in an at least partially interleaved or overlapping configuration when appropriately aligned.

In one example the second mechanical code may pass through the first mechanical code or vice versa. Thus when arriving in the expelling position the first mechanical code and the second mechanical code may either be mutually mechanically engaged, e.g., rotationally locked or one of the first and second mechanical codes has passed through the other one of the first and second mechanical codes. In the latter case first and second mechanical codes may be mechanically disengaged when arriving in the expelling position. In one example of a dose setting position the second mechanical code is located distally from the first mechanical code. When properly aligned the second mechanical code may pass through the first mechanical code thus arriving at a distal side of the first mechanical code when the expelling position of at least one of the rotatable member and the counterpart member has been reached.

When appropriately aligned the first and the second mechanical code enable a longitudinal displacement of at least one of the rotatable member and the counterpart member towards and into the expelling position over a mode switching distance. The mode switching distance is larger than a distance at least one of the rotatable member and the counterpart member can be moved in longitudinal direction relative to the other one of the rotatable member and the counterpart member when the first and the second mechanical codes are out of alignment. When the first mechanical code is appropriately aligned to the second mechanical code the distance the at least one of the rotatable member and the counterpart member can be displaced in longitudinal direction towards the expelling position is at a maximum. This maximum distance is larger than or equal to the mode switching distance that is required for switching the injection device from the dose setting mode into the dose expelling mode.

In another example the injection device further comprises a dispensing spring that is compressible along the longitudinal direction. The dispensing spring is further engaged with one of the rotatable member and the counterpart member. It may be directly or indirectly engaged with one of the rotatable member and the counterpart member. The rotatable member or the counterpart member is displaceable along the longitudinal direction from a dose setting position into the dose expelling position against the action of the dispensing spring. The dispensing spring is thus configured to return the rotatable member or the counterpart member from the dose expelling position towards and into the dose setting position.

In other words, in an initial configuration and as a user grabs the injection device for setting of a dose the rotatable member or the counterpart member is located in a dose setting position. It may be permanently kept or urged into the dose setting position by the dispensing spring. It may be then displaceable into the dose expelling position against the action of the dispensing spring supposed that the first and the second mechanical codes are correctly aligned. Typically, that one of the rotatable member and the counterpart member that is longitudinally displaceable under the action of the dispensing spring is also mechanically engageable with the trigger.

Typically, the trigger is also displaceable along the longitudinal direction from the dose setting position into the dose expelling position against the action of the dispensing spring. Both, the trigger as well as the rotatable member or the counterpart member are displaceable from the dose expelling position into the initial dose setting position under the action of the dispensing spring. The dispensing spring may comprise a longitudinally extending compression spring that is configured to induce a longitudinal displacement of at least one of the rotatable member, the counterpart member and the trigger towards the initial dose setting position. Typically, the dose setting position is a proximal position and the dose expelling position is a distal position. As the rotatable member, the counterpart member or the trigger is displaced from the dose setting position into the dose expelling position it is subject to a distally directed displacement. As for instance the trigger is released the at least one of the rotatable member, the counterpart member and the trigger is displaced in the opposite direction, i.e., the proximal direction into the dose setting position.

In a further example at least one of the rotatable member and the trigger is kept in a proximal dose setting position under the action of the dispensing spring. In this way, dialling or setting of a dose accompanied by a respective rotation of the rotatable member relative to the housing and relative to the counterpart member can be induced by a user immediately, i.e., without any further manipulation of at least one of the rotatable member, the counterpart member or the trigger.

According to a further example the first mechanical code and the second mechanical code each comprise at least a first code feature. The first code feature comprises at least one of a protrusion and a recess. Typically, the first mechanical code comprises one or more of such code features and the second mechanical code comprises one or more of such code features. The code features of the first mechanical code are complementary-shaped to the code features of the second mechanical code. For instance, when the first mechanical code comprises a first code feature having a protrusion the second mechanical code comprises a first code feature having a recess matching with the protrusion of the first mechanical code. A code feature may further comprise not only a single protrusion and a single recess but may also comprise a sequence or pattern of at least one protrusion and at least one recess. The second mechanical code matching with the first mechanical code comprises a corresponding sequence or pattern of protrusions and recesses.

When in the dose setting position the at least one protrusion or recess of the first mechanical code may be aligned to but out of engagement to a correspondingly shaped recess or protrusion of the second mechanical code.

As the at least one of the rotatable member and the counterpart member is subject to a longitudinal displacement towards the expelling position the at least one protrusion or recess of the first mechanical code engages with, slides into or slides through at least one recess or protrusion of the second mechanical code; and vice versa.

Typically, the at least one protrusion of a first code feature of one of the first mechanical code and the second mechanical code comprises an abutment face by way of which the protrusion may axially or longitudinally abut with an abutment face of the other one of the first mechanical code and the second mechanical code. In this way and if for instance a protrusion of the first mechanical code is out of alignment with a recess of the second mechanical code the protrusion will abut with the second mechanical code as the at least one of the rotatable member and the counterpart member is moved towards the expelling position. As soon as the abutment face of the protrusion of one of the first mechanical code and the second mechanical code abuts with the other one of the first mechanical code and the second mechanical code a further axial or longitudinal displacement of the rotatable member relative to the counterpart member is blocked and impeded.

According to a further example the first mechanical code and the second mechanical code each comprise at least a second code feature comprising at least one of a protrusion and a recess. In other words, each of the first mechanical code and the second mechanical code comprises a first code feature and at least a second code feature and optionally even a third code feature, a fourth code feature or even further code features. Each one of the code features of the first mechanical code and the second mechanical code comprises at least one of a protrusion and a recess. The code features may comprise only one protrusion or only one recess. One of the first and second code features may also comprise both, a protrusion and a recess or even a sequence of protrusions and recesses. Typically and according to another example the first and the second code features are arranged at a predefined angular distance from each other on a circumference of at least one of the counterpart member and the rotatable member.

By having numerous code features the first and second mechanical code may be distributed and spread along the circumference of at least one of the counterpart member and the rotatable member. In this way, an increased abutment between the rotatable member and the counterpart member can be achieved and blocking forces to be transferred between the first and the second mechanical codes in case of an alignment mismatch can be reduced.

Maximum blocking forces to be provided by the first and the second mechanical codes in case of an out of alignment configuration can be effectively distributed across multiple code features of the first mechanical code and the second mechanical code. With more than just one code feature it may be of further benefit when the rotatable member and the counterpart member are rotationally lockable or rotationally engageable when arriving in the expelling position. Then, a torque or a force transferred from the rotatable member to the counterpart member can be split among the numerous code features of first and second mechanical codes.

First and second code features can be arranged at a predefined angular distance from each other on an inner circumference or on an outer circumference of at least one of the counterpart member and the rotatable member. When for instance the counterpart member is insertable into a hollow-shaped rotatable member the code features of the counterpart member are typically provided on the outer circumference of the counterpart member and the code features of the rotatable member are provided on an inside circumference or inner circumference of the rotatable member. The code features of the counterpart member may be located on an outside sidewall of a sleeve-shaped counterpart member. The code features of the rotatable member may be provided on an inside sidewall of a receptacle or of a hollow portion of the rotatable member. With other examples it might be the rotatable member that is received inside a hollow section or hollow receptacle of the counterpart member. Then, the code features of the counterpart member are provided on an inner circumference of the counterpart member, hence at an inside facing sidewall section thereof and the code features of the rotatable member are provided on an outside surface, hence on an outer circumference of the rotatable member.

The first mechanical code may be provided at a longitudinal end of the counterpart member that faces towards the rotatable member. Accordingly, the second mechanical code may be provided on a longitudinal end of the rotatable member that faces towards the counterpart member.

When the rotatable member is for instance implemented as the trigger the first mechanical code may be provided at a distal end thereof. Here, the counterpart member may be provided or integrated in a proximal portion of the housing, e.g., at a proximal end of the housing.

According to another example at least one of the first mechanical code and the second mechanical code comprises at least two or more code features equidistantly or equiangularly arranged on the circumference of at least one of the counterpart member and the rotatable member. An equidistant or equiangular arrangement of two or more code features on the circumference, e.g., on an inner circumference or an outer circumference of at least one of the counterpart member and the rotatable member has the benefit that the counterpart member and the rotatable member may engage via the first mechanical code and the second mechanical code when appropriately aligned.

By increasing the number of mutually engaging code features of the counterpart member and the rotatable member a total strength and stability of the mechanical engagement provided by the first and the second mechanical codes can be improved. A rather robust and stable mechanical engagement between first and second mechanical codes can thus be provided. This may be of advantage when for instance the rotatable member and the counterpart member are rotationally locked in the expelling position and wherein the rotational interlock between the first mechanical code and the second mechanical code is configured to transfer an angular momentum across the interface of the rotatable member and the counterpart member when in the expelling position.

With equidistantly and equally-shaped code features the number of allowable alignment configurations of first and second mechanical codes per revolution of the rotatable member relative to the counterpart member increases accordingly. With two code features there will be two of the rotational states of the rotatable member in which the first and the second mechanical codes are in longitudinal alignment. With three identically-shaped and equidistantly or equiangularly arranged code features there will be three rotational states of the rotatable member in which the first and the second mechanical codes are appropriately aligned and so on.

The two or more code features of one of the first and second mechanical codes may be equally shaped or may be differently shaped. With two identically shaped and equidistantly or equiangularly arranged code features on the first mechanical code and on the second mechanical code there will be two rotational states of the rotatable member per revolution at which the first and the second mechanical code are aligned. With three identically shaped and equidistantly or equiangularly arranged code features on the first mechanical code and on the second mechanical code three alignment configurations of the first and the second mechanical codes per revolution of the rotatable member will be obtained starting from which the injection device can be switched into the dose expelling mode. With differently shaped first and second code features or with a non-equidistant or non-equiangular separation of the code features there may be only one allowable alignment configuration of first and second mechanical codes per revolution of the rotatable member.

According to a further example the at least one protrusion is a radial protrusion and the at least one recess is a radial recess. With a radial inwardly extending protrusion the recess also extends radially inwardly. With a radially outwardly extending protrusion the complementary-shaped radial recess also extends radially outwardly. The radial protrusion comprises a cross-section that matches with the cross-section of the radial recess. If the first mechanical code is correctly aligned to the second mechanical code the radial protrusion may slide into the complementary-shaped radial recess as at least one of the rotatable member and the counterpart member is subject to a longitudinal displacement towards the expelling position.

In the expelling position the radial protrusion may still be located inside the radial recess or may have passed through the radial recess in longitudinal direction. When the radial protrusion remains engaged with the radial recess upon arriving in the expelling position the rotatable member and the counterpart member may be rotationally engaged or rotationally locked. Hence, any further rotation of the rotatable member or of the counterpart member may be equally and hence unalteredly transferred to the other one of the rotatable member and the counterpart member.

With another example the radial protrusion may be located at a longitudinal distance from the radial recess on a first side of the radial recess. As the at least one of the rotatable member and the counterpart member is moved into the expelling position the radial protrusion may have passed through the radial recess and may then be located on an opposite, hence on a second side of the radial recess. In this example the rotatable member and the counterpart member may be free to rotate relative to each other even when arriving in the expelling position and when the injection device has been switched into the dose expelling mode.

According to a further example the radial protrusion comprises an elongated rib extending along the longitudinal direction and/or wherein the radial recess comprises an elongated groove extending along the longitudinal direction. In other words, the radial protrusion and the elongated rib are configured to form a splined engagement of the rotatable member and the counterpart member. For this it is only necessary, that one of the protrusion and the recess is of elongated shape along the longitudinal direction. With at least one of an elongated rib and an elongated groove a torque-proof engagement between the first and second mechanical codes as well as between the rotatable member and the counterpart member can be established and obtained as soon as the rib or protrusion enters the recess or elongated groove. With at least one of an elongated rib or elongated groove the rotatable member of the counterpart member may be subject to a longitudinal relative displacement while a rotational coupling therebetween is maintained.

According to another example the at least one protrusion is an axial protrusion extending along the longitudinal direction. The at least one recess is correspondingly shaped and comprises an axial recess extending along the longitudinal direction. There may be provided numerous axial protrusions and axial recesses on the first mechanical code and on the second mechanical code. Here, the first mechanical code and the second mechanical code may be provided on an end face or on a distally or proximally facing flange section of the rotatable member and/or of the counterpart member, respectively.

For instance, the axial protrusion and/or the axial recess of the code feature of at least one of the first and second mechanical codes may be provided on an end face of at least one of the rotatable member and the counterpart member, which end face faces in longitudinal direction, e.g., in proximal direction or distal direction. Such axially extending and mutually engaging code features are of particular benefit for implementation with a rotatable member or a counterpart member having a comparatively thin sidewall. For a radial recess the thickness of the sidewall must be at least somewhat larger than the radial depth of the radial recess.

In another example at least one of the axial protrusion and the axial recess comprises a tapered or toothed structure pointing in the longitudinal direction. Typically, the first mechanical code comprises both, at least one axial protrusion and at least one axial recess. The second mechanical code also comprises both, at least one of an axial protrusion and an axial recess complementary-shaped to the axial protrusion and the axial recess of the first mechanical code. A tapered or toothed structure of at least one of the axial protrusion and the axial recess further provides a limited circumferential guiding functionality as the first mechanical code approaches the second mechanical code in longitudinal direction. In the event that the first mechanical code should not be absolutely exactly angularly aligned to the second mechanical code the tapered or toothed structure of the mutually corresponding axial protrusion and axial recess may provide and induce a further, rather small rotation of at least one of the rotatable member and the counterpart member as one of the rotatable member and the counterpart member is displaced longitudinally towards the expelling position.

The tapered or toothed structure pointing in longitudinal direction of first and second mechanical codes also provides a torque-proof engagement of the rotatable member with the counterpart member. If the axial protrusion is sized to entirely fill the axial recess the rotatable member is effectively lockable to the counterpart member as the expelling position has been reached. Also here, and by means of the at least one axial protrusion and the at least one axial recess of first and second mechanical codes the respective mechanical codes, hence the rotatable member and the counterpart member can be rotationally locked. This is of particular benefit to impede a rotation of the rotatable member during a dose expelling procedure.

For instance, at least one of the axial protrusion and the axial recess may be provided on the trigger configured as the rotatable member and the other one of the axial protrusion and the axial recess may be provided on the housing of the injection device. Once the rotatable member, hence the trigger, is depressed in the distal direction thus arriving in the expelling position the trigger may be locked against rotation relative to the housing through the mutually corresponding and inter-engaging protrusion and recess.

According to a further example at least one of the first mechanical code and the second mechanical code may comprise a crown wheel or a crown gear. The crown wheel or crown gear may be interrupted so as to exhibit one of the first or second mechanical codes. For instance, the crown gear on one of the rotatable member and the counterpart member may be interrupted and may comprise a rather flat-shaped abutment face thus representing a section of the crown gear that is void of an axial recess. If improperly aligned or if the first and the second mechanical codes are out of alignment axially protruding teeth of one of the rotatable member and the counterpart member will face the abutment or abutment face of the other one of the rotatable member and the counterpart member thus impeding a longitudinal displacement of at least one of the rotatable member and the counterpart member relative to the other one of the rotatable member and the counterpart member. The teeth cannot engage and prevent a further longitudinal displacement of the rotatable member or counterpart member towards the expelling position.

According to another example the counterpart member and the rotatable member are rotationally connectable or rotationally lockable to each other through the first mechanical code and the second mechanical code. This can be achieved either by a radial protrusion and a radial recess provided on the rotatable member and the counterpart member. This can be alternatively achieved by at least one axial protrusion and at least one axial recess on the rotatable member and on the counterpart member. In either way the rotatable member and the counterpart member can be rotationally engaged as the first and the second mechanical codes are mutually aligned and when the rotatable member and the counterpart member are subject to a longitudinal displacement relative to each other to reach the expelling position.

The first and the second mechanical code therefore has two functions. As long as the rotatable member is in a discrete rotational state that does not match with a predefined rotational state coincides with a predefined size of a dose to be expelled, the first and second mechanical codes prevent and impede a longitudinal displacement of at least one of the rotatable member and the counterpart member towards and into the expelling position. In effect the injection device cannot be switched from the dose setting mode into the dose expelling mode. Furthermore and when the rotatable member is in a predefined rotational state of the range of numerous rotational states in which the first mechanical code is longitudinally aligned with the second mechanical code, the mechanical codes enable a displacement of at least one of the rotatable member and the counterpart member by a mode switching distance thus arriving in an expelling position in which the rotatable member and the counterpart member are rotationally locked to each other through the first and the second mechanical code.

In another example the counterpart member and the rotatable member are rotationally locked when one of the rotatable member and the counterpart member reaches the expelling position. When reaching the expelling position the rotatable member and the counterpart member May be also in axial abutment by the first mechanical code and the second mechanical code. Here, the first mechanical code and the second mechanical code may also provide a longitudinal abutment between the rotatable member and the counterpart member. When rotationally locked in the expelling position a torque applied to one of the rotatable member and the counterpart member is transferred to the other one of the rotatable member and the counterpart member. If for instance the counterpart member is steadfastly connected to the housing the rotatable member will be rotationally secured to the housing when reaching the expelling position.

According to a further example the counterpart member is integrated into the housing or the counterpart member is steadfastly connected to the housing. Here, the rotatable member is formed by the trigger or it is displaceable in longitudinal direction relative to the housing by depressing of the trigger in the distal direction. With this example the first code may be provided at a proximal end of the housing. The second code may be provided at a distal end of the trigger. The trigger may comprise a sidewall section or a skirt and the second mechanical code may be provided on the sidewall or skirt of the trigger. Moreover, the first mechanical code may comprise a sequence of axial recesses and protrusions along the circumference of a proximal front face of the housing. Accordingly, also the trigger may comprise a sequence of axially extending protrusions and recesses along the circumference of the sidewall or skirt. In other words, the trigger may comprise a distally facing crown wheel section or crown wheel portion and the housing may comprise a correspondingly shaped proximally facing crown wheel section or crown wheel portion. In this way the trigger can be rotationally locked to the housing when depressed in distal direction towards and into the expelling position.

In a further example the injection device comprises a dose indicator and a drive sleeve. The dose indicator may form the rotatable member and is threadedly engaged with the housing. Here, the drive sleeve may form the counterpart member and may be displaceable in longitudinal direction relative to the housing by depressing of the trigger in the distal direction. With this example the rotatable member is rotatable but is axially constrained and/or axially fixed to the housing. The counterpart member, formed by the drive sleeve is rotationally locked to the housing and cannot rotate relative to the housing as long as the device is in the dose setting mode. Here, the drive sleeve and the dose indicator may constitute a splined engagement provided by the first and the second mechanical code. The drive sleeve and the dose indicator may comprise at least one pair of mutually corresponding radial protrusions and recesses along the inner and outer circumference thereof.

Typically, the drive sleeve is located radially inside the dose indicator. The dose indicator at least in sections comprises a hollow structure to receive at least a portion of the drive sleeve. On an outside surface of the drive sleeve there is provided at least one radial recess or protrusion to engage with a correspondingly shaped radial recess on the inside surface of the dose indicator. The dose indicator is subject to a rotation during setting of the dose while the drive sleeve is rotationally locked to the housing during dose setting. If a dose of appropriate or predefined size has been set or dialled the second mechanical code of the dose indicator longitudinally aligns with the first mechanical code of the counterpart member, e.g., the drive sleeve thus enabling a longitudinal displacement of the drive sleeve relative to the dose indicator.

The longitudinal displacement of the drive sleeve, typically in distal direction towards the expelling position is inducible by the trigger. When displacing the drive sleeve distally towards and into the expelling position a torque-proof engagement between the drive sleeve and the dose indicator may be established via the first mechanical code and the second mechanical code. When the expelling mechanism is implemented as a wind up expelling mechanism one of the drive sleeve and the dose indicator may be engaged with a mechanical energy reservoir, such as a helically wound torsion spring. Such a mechanical energy reservoir may be connected with one end to the housing and may be further connected with an opposite end to one of the dose indicator and the drive sleeve. As soon as a torque-proof engagement between the drive sleeve and the dose indicator has been established, thereby engaging a clutch, mechanical energy from the mechanical energy reservoir may be released by releasing of another clutch or clutch mechanism. Under the action of a depleting mechanical energy reservoir the dose indicator may then be subject to a dose decrementing rotation relative to the housing, which rotation is equally transferred to the drive sleeve thus transferring a driving force to the piston rod for urging against the bung of the cartridge.

According to another example the injection device comprises the cartridge that contains the medicament. The cartridge is arranged inside the housing. The injection device may be configured or implemented as a disposable injection device intended to be discarded in its entirely once the medicament has been expelled through a distal outlet of the cartridge, e.g., through a needle assembly penetrating a seal at the distal end of the cartridge.

In the present context a distal end or distal direction refers to that end section of the injection device from which the liquid medicament is expelled. The proximal end or proximal direction refers to that end section of the injection device which is furthest away from biological tissue of a patient to be treated with the medicament. The injection device is typically configured for administration of a liquid medicament, such as insulin or heparin. The injection device is typically configured for self-medication. It is configured for operation by only one hand of a user. The trigger typically provided at the proximal end of the injection device is configured to be depressed by a thumb of a user while residual fingers of the same hand may grip the housing of the injection device.

The injection device may comprise a cartridge containing a liquid drug or medicament. In instances, by pressing the injection button a portion thereof may be expelled from the cartridge according to the dialled or pre-set amount. The terms "drug" and "medicament", may refer to a pharmaceutical formulation containing at least one pharmaceutically active compound. More details on particular pharmaceutical formulations may be taken from the disclosure of the co-pending application PCT/EP2018/082640, which, to this extent, shall be included herein by reference.

It will be further apparent to those skilled in the art that various modifications and variations can be made to the present invention without departing from the scope of the present disclosure as it is defined by the claims. Further, it is to be noted, that any reference numerals used in the appended claims are not to be construed as limiting the scope of the invention.

BRIEF DESCRIPTION OF THE FIGURES

In the following various embodiments of a data collection device in connection with an injection device are described by making reference to the drawings, in which:

FIG. 1 shows a top view of the drug delivery device of the present disclosure in the minimum dose position;

FIG. 2 shows an exploded view of the components of the device of FIG. 1;

FIG. 3 shows a sectional view of the device of FIG. 1;

FIG. 4a shows an enlarged sectional view of a detail of the device of FIG. 1 in the dose setting mode;

FIG. 4b shows an enlarged sectional view of a detail of the device of FIG. 1 in the dose dispensing mode;

FIGS. 5a, b show an interface between the number sleeve and the button of the device of FIG. 1;

FIG. 6 shows an interface between the housing and the button of the device of FIG. 1;

FIGS. 7a, b show an interface between the number sleeve and the drive sleeve of the device of FIG. 1 in the dose setting mode and in the dose dispensing mode;

FIG. 8 shows an interface between the piston rod and a bearing of the device of FIG. 1;

FIG. 10 shows in a sectional view the components of an end of dose clicker of the device of FIG. 1;

FIG. 15 shows a further portion of the number sleeve of the device of FIG. 1;

FIG. 16 shows a portion of the drive spring of the device of FIG. 1;

FIGS. 17a, b show top views of the device of FIG. 1 with 0 units dialled and with 96 units dialled;

FIG. 18 shows an interface between the housing and the drive sleeve of the device of FIG. 1;

FIGS. 19a, b show an interface between the clutch plate and the drive sleeve of the device of FIG. 1;

FIG. 20 shows a last dose mechanism of the device of FIG. 1;

FIG. 21 shows the torsion spring of the device of FIG. 1; and

FIGS. 22*a-c* show different embodiments of the threads between the piston rod and the housing of the device of FIG. 1.

DETAILED DESCRIPTION

Figures 9A, 9B, 11A, 11B, 11C:
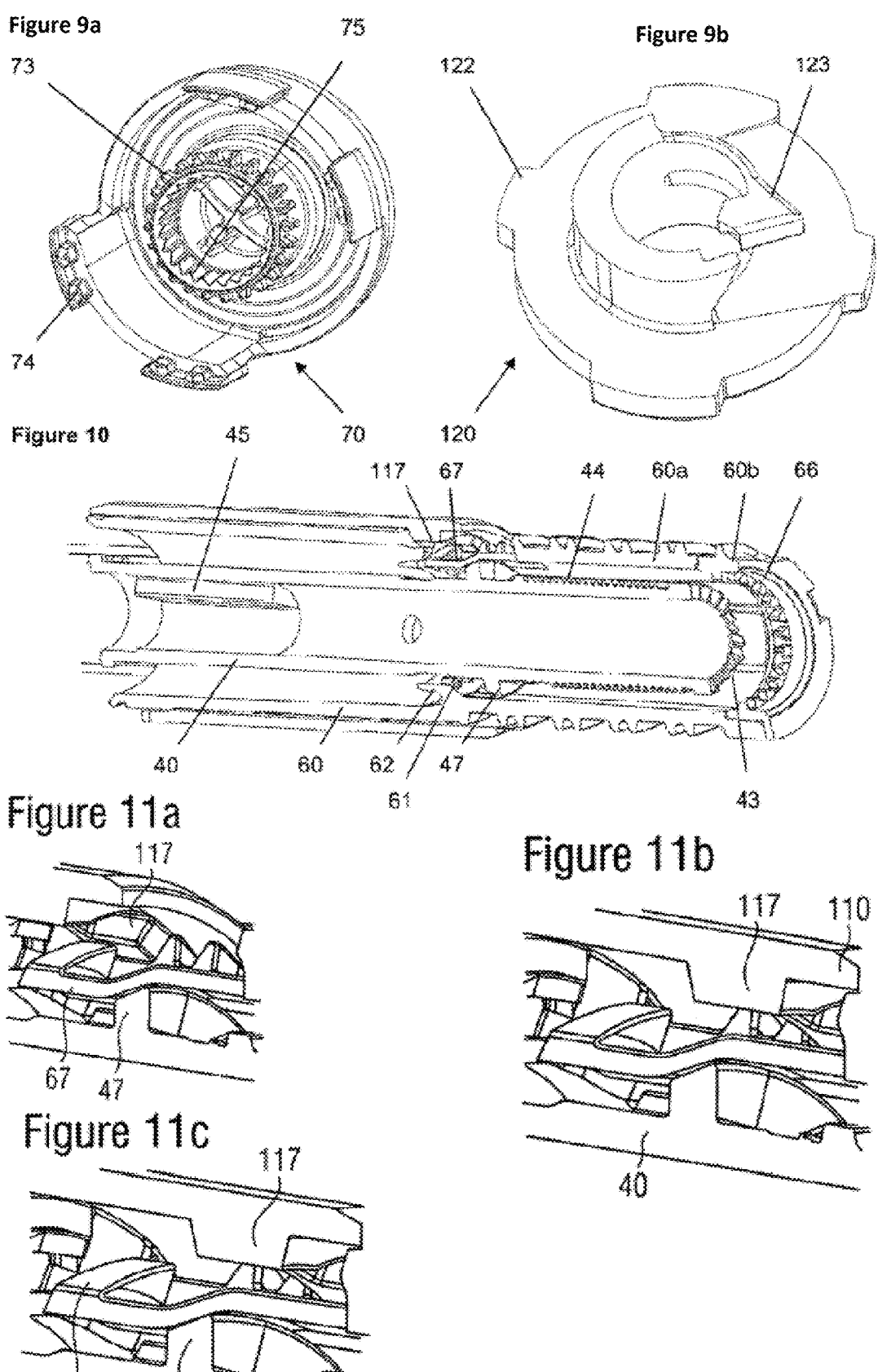
FIGS. 9a, b show an interface between the clutch plate and the button of the device of FIG. 1.
FIGS. 11a-c show in enlarged views the sequence of generating a click at the end of dose dispensing of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element having a proximal end with an enlarged diameter. The housing 10 provides location for the liquid medication cartridge 100 and cartridge holder 20, windows 11*a*, 11*b* for viewing the dose number on the number sleeve 60 and the gauge element 110, and a feature on its external surface, e.g., a circumferential groove, to axially retain the dose selector 80. A flange-like or cylindrical inner wall 12 comprises an inner thread engaging the piston rod 30. The housing 10 further has at least one internal, axially orientated slot or the like for axially guiding the gauge element 110. In the embodiment shown in the Figures, the distal end is provided with an axially extending strip 13 partly overlapping cartridge holder 20. The Figures depict the housing 10 as a single housing component. However, the housing 10 could comprise two or more housing components which may be permanently attached to each other during assembly of the device.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the inner wall 12 of housing 10. The lead screw 30 is an elongate member with an outer thread 31 (FIG. 3) engaging the corresponding thread of the inner wall 12 of housing 10. The thread 31 may have a large lead-in, for example a wedge shape form, at its distal end to engage a corresponding housing thread form on the first rotation. The interface comprises (i) at least one longitudinal groove or track and (ii) a corresponding protrusion or spline 45, where spline 46 is included in the driver 40, as illustrated in, e.g., FIG. 10. At its distal end, the lead screw 30 is provided with an interface for clip attachment of the bearing 140. In the present embodiment, this interface comprises two clip arms 32 extending in the distal direction defining an insertion space between them for insertion of a bearing 140 interface. As an alternative, the interface may comprise only one single clip arm extending more than 180° about the longitudinal axis, or may comprise one or several clip arms 32. The clip arm(s) 32 may have a bent form with a recessed clip portion as shown in FIG. 8. Preferably, the clip arm(s) form a cylindrical outer face having a diameter equal to or smaller than the outer diameter of the lead screw at the base of the groove (flute base) of the outer thread 31. A concave contact surface 33 is provided between the clip arms 32 for abutment of a corresponding portion of bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

A splined interface between the housing 10 and the drive sleeve 40 serves to prevent a rotation of the drive sleeve 40 during dose setting. This interface, which is shown in FIG. 18 in detail, comprises a ring of radially extending outer teeth 41 at the distal end of the drive sleeve 40 and further comprises corresponding radially extending inner teeth 14 of the housing 10. When the button 70 is pressed, these drive sleeve 40 to housing 10 spline teeth 14, 41 are disengaged allowing the drive sleeve 40 to rotate relative to housing 10.

A further splined tooth interface with the number sleeve 60 is not engaged during dialling, but engages when the button 70 is pressed, preventing relative rotation between the drive sleeve 40 and number sleeve 60 during dispense. In the preferred embodiment shown in FIGS. 7*a* and 7*b* this interface comprises inwardly directed splines 61 on a flange 62 on the inner surface of the number sleeve 60 and a ring of radially extending outer splines 42 of drive sleeve 40. The corresponding splines 61, 42 are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

Preferably, the splines 61, 42 are arranged such that they are decoupled when teeth 41 of drive sleeve 40 and inner teeth 14 of housing component 10 mesh and engage when teeth 41 and inner teeth 14 disengage. In a preferred embodiment the splines 61, 42 are longer in the axial direction compared with teeth 41, 14. This allows engagement of the splines 61, 42 shortly before disengagement of teeth 41, 14. In other words, the splines 61, 42 and the teeth 41, 14 are designed and arranged such that actuation of the button 70 rotationally constrains the drive sleeve 40 to the number sleeve 60 before the drive sleeve 40 is allowed to rotate relative to housing 10. Similarly, as the button 70 is released after dose dispensing axial movement of the drive sleeve 40 first rotationally constrains the drive sleeve 40 to the housing and thereafter decouples splines 61, 42. As an alternative to the corresponding splines 61, 42 teeth may be provided. As a further alternative or in addition to splines 61, 42, drive sleeve 40 and number sleeve 60 may be rotationally coupled to each other during dose dispensing via clutch plate 120.

An interface of the drive sleeve 40 which is shown in FIGS. 19*a* and 19*b* comprises a ring of ratchet teeth 43 located at the proximal end face of drive sleeve 40 and a ring of corresponding ratchet teeth 121 of clutch plate 120.

The driver 40 has a threaded section 44 providing a helical track for the nut 50 (FIG. 20). In addition, a last dose abutment or stop 46 is provided which may be the end of the thread 44 track or preferably a rotational hard stop for interaction with a corresponding last dose stop 51 of nut 50, thus limiting movement of the nut 50 on the thread 44. At least one longitudinal spline 45 engages a corresponding track of the lead screw 30. Further, the drive sleeve is provided with a ramp 47 interacting with a clicker arm 67 when the drive sleeve 40 is in its distal position during dose dispensing, i.e., when button 70 is depressed.

The last dose nut 50 is located between the number sleeve 60 and the drive sleeve 40. It is rotationally constrained to the number sleeve 60, via a splined interface (splines 52 on nut 50). It moves along a helical path relative to the drive sleeve 40, via a threaded interface (thread 44), when relative rotation occurs between the number sleeve 60 and drive sleeve 40 which is during dialling only. This is shown in FIG. 20. As an alternative, the nut 50 may be splined to the driver 40 and threaded to the number sleeve 60. In the embodiment shown in the Figures, the nut 50 is a full nut, but in alternative embodiments it may be a half nut, i.e., a component extending approximately 180° around the center axis of the device. A last dose stop 51 is provided engaging stop 46 of drive sleeve 40 when a dose is set corresponding to the remaining dispensable amount of medicament in the cartridge 100.

The dose indicator or number sleeve 60 is a tubular element as shown in FIGS. 2 and 3. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member.

For manufacturing reasons the number sleeve 60 of the embodiment shown in the Figures comprises a number sleeve lower 60*a* which is rigidly fixed to a number sleeve upper 60*b* during assembly to form the number sleeve 60. Number sleeve lower 60*a* and number sleeve upper 60*b* are separate components only to simplify number sleeve 60 mould tooling and assembly. As an alternative, the number sleeve 60 may be a unitary component. The number sleeve 60 is constrained to the housing 10 by features towards the distal end to allow rotation but not translation. The number sleeve lower 60*a* is marked with a sequence of numbers, which are visible through the gauge element 110 and the openings 11*a*, 11*b* in the housing 10, to denote the dialled dose of medicament.

Further, the number sleeve lower 60*a* has a portion with an outer thread 63 engaging the gauge element 110. End stops 64, 65 are provided at the opposite ends of thread 63 to limit relative movement with respect to the gauge element 110.

Clutch features which have the form of a ring of splines 66 in the embodiment of FIG. 5*b* are provided inwardly directed on number sleeve upper 60*b* for engagement with splines 73 of the button 70 during dose setting and dose correction. A clicker arm 67 is provided on the outer surface of number sleeve 60 which interacts with the drive sleeve 40 and the gauge member 110 for generating a feedback signal. In addition, the number sleeve lower 60*a* is rotationally constrained to the nut 50 and to the clutch plate 120 via a splined interface comprising at least one longitudinal spline.

An interface for attachment of the torsion spring 90 to the number sleeve lower 60*a* comprises large lead-ins and a groove feature 68 with a pocket 69 or anchor point for receiving a first coil or hook portion of the spring. The groove 68 has an end feature in the form of a ramp that is in interference with the hook portion 91 of the spring. The design of the groove 68 is such that the spring 90 may be received within the pocket 69 without interfering with the gauge element 110.

The button 70 which forms the proximal end of the device is permanently splined to the dose selector 80. A central stem 71 extends distally from the proximal actuation face of the button 70. The stem 71 is provided with a flange 72 carrying the splines 73 for engagement with splines 66 of the number sleeve upper 60*b* (FIGS. 5*a* and 5*b*). Thus, it is also splined via splines 66, 73 (FIGS. 5*a* and 5*b*) to the number sleeve upper 60*b* when the button 70 is not pressed, but this spline interface is disconnected when the button 70 is pressed. The button 70 has a discontinuous annular skirt with splines 74. When the button 70 is pressed, splines 74 on the button 70 engage with splines on the housing 10 (FIG. 6), preventing rotation of the button 70 (and hence the dose selector 80) during dispense. These splines 74, 15 disengage when the button 70 is released, allowing a dose to be dialled. Further, a ring of ratchet teeth 75 is provided on the inner side of flange 72 (FIGS. 9*a*, 9*b*) for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. As shown in FIG. 16, the spring has a hook 91 at one end for attachment on the number sleeve 60. A similar hook end 92 is provided at the opposite end for attachment on the housing 10. The torsion spring 90 is pre-wound upon assembly, such that it applies a torque to the number sleeve 60 when the mechanism is at zero units dialled. The action of rotating the dose selector 80, to set a dose, rotates the number sleeve 60 relative to the housing 10, and charges the torsion spring 90 further.

The torsion spring 90 is formed from a helical wire with at least two different pitches. In FIG. 21, both ends are formed from 'closed' coils 93, i.e., the pitch equals the wire diameter and each coil contacts the adjacent coil. The central portion has 'open' coils 94, i.e., the coils do not contact each other.

The cartridge 100 is received in cartridge holder 20 (FIG. 3). The cartridge 100 may be a glass ampoule having a moveable rubber bung 101 at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature 111 on its inner surface which engages with the helical thread cut in the number sleeve 60 such that rotation of the number sleeve 60 causes axial translation of the gauge element 110.

This helical feature on the gauge element 110 also creates stop abutments 112, 113 against the end of the helical cut in the number sleeve 60 to limit the minimum and maximum dose that can be set.

The gauge element 110 has a generally plate or band like component having a central aperture 114 or window and two flanges 115, 116 extending on either side of the aperture. The flanges 115, 116 are preferably not transparent and thus shield or cover the number sleeve 60, whereas the aperture 114 or window allows viewing a portion of the number sleeve lower 60a. Further, gauge element 110 has a cam 117 and a recess 118 (FIGS. 11a-12c) interacting with the clicker arm 67 of the number sleeve 60 at the end of dose dispensing.

As can be seen in FIGS. 9a/b and 19a/b, the clutch plate 120 is a ring-like component. The clutch plate 120 is splined to the number sleeve 60 via splines 122. It is also coupled to the drive sleeve 40 via a ratchet interface (ratchet teeth 43, 121). The ratchet provides a detented position between the number sleeve 60 and drive sleeve 40 corresponding to each dose unit, and engages different ramped tooth angles during clockwise and anti-clockwise relative rotation. A clicker arm 123 is provided on the clutch plate 120 for interaction with ratchet features 75 of the button.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface (ratchet teeth 43, 121) is always engaged. In the 'at rest' position, it also ensures that the button splines 73 are engaged with the number sleeve splines 66, and the drive sleeve teeth 41 are engaged with teeth 14 of the housing 10.

The bearing 140 is axially constrained to the piston rod 30 and acts on the bung 101 within the liquid medicament cartridge. It is axially clipped to the lead screw 30, but free to rotate. The bearing 140 comprises a disc 141 having a stem 142 extending in the proximal direction. The stem 142 has at its proximal end a convex contact surface 143. In addition, a recessed portion 144 is provided on the stem 142. The curvature of the convex contact surface 143 and the concave contact surface 33 is chosen such that the contact diameter between the bearing 140 and lead screw 30 is small to minimize the frictional losses at this interface. The design of the clip interface between bearing 140 and lead screw 30 permits the lead screw 30 to be assembled axially, from the proximal end and through the thread engagement to the housing 10, which simplifies assembly. In addition, this design allows a simple "open and shut" mould tooling for both components.

With the device in the 'at rest' condition as shown in FIGS. 4a and 17a, the number sleeve 60 is positioned against its zero dose abutment 64, 113 with the gauge element 110 and the button 70 is not depressed. Dose marking '0' on the number sleeve 60 is visible through the windows 11b and 114 of the housing 10 and gauge element 110, respectively.

The torsion spring 90, which has a number of pre-wound turns applied to it during assembly of the device, applies a torque to the number sleeve 60 and is prevented from rotating by the zero dose abutment 64, 113. It is also possible to 'back-wind' the mechanism slightly due to an offset between the zero dose stop 64, 113 and the angular offset of the drive sleeve 40 spline teeth. This has the effect of preventing possible weepage when a dose is dialled and the zero dose abutment is disengaged.

The automated assembly of the torsion spring 90 into the number sleeve 60 can be achieved by incorporating large lead-ins and a groove feature to the number sleeve 60. As the torsion spring 90 is rotated during assembly, the hook end form 91 locates in the groove feature before engaging the anchor point in the number sleeve 60. To help to prevent the torsion spring 90 disengaging the anchor point 69 during subsequent assembly steps it is possible to create an interference between the torsion spring 90 and the number sleeve 60, or a one-way clip feature.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialled dose. The gauge element 110 has flanges 115, 116 either side of the window area 114 which cover the numbers printed on the number sleeve 60 adjacent to the dialled dose to ensure only the set dose number is made visible to the user.

A specific feature of this disclosure is the inclusion of a visual feedback feature in addition to the discrete dose number display typical on devices of this type. The distal end (flange 115) of the gauge element 110 creates a sliding scale through a small window 11a in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

The openings 11a, 11b in the housing 10 allow the user to view the gauge feature and number display as shown in FIGS. 17a and 17b. To reduce dust ingress and prevent the user from touching moving parts, these openings 11a, 11b are covered by translucent windows. These windows may be separate components, but in this embodiment they are incorporated into the housing 10 using 'twin-shot' moulding technology. A first shot of translucent material forms the internal features and the windows 11a, 11b, and then a 'second shot' of opaque material forms the outer cover of the housing 10.

The mechanism utilises a dose selector 80 with an increased diameter relative to the housing 10 which aids dialling although this is not a requirement of the mechanism. This feature is particularly useful (but not essential) for an auto-injector mechanism where a power supply is charged during dose setting and the torque required to turn the dose selector 80 may be higher than for a non-auto injector device.

The drive sleeve 40 is prevented from rotating as the dose is set and the number sleeve 60 rotated, due to the engagement of its splined teeth 41 with teeth 14 of the housing 10. Relative rotation must therefore occur between the clutch plate 120 and drive sleeve 40 via the ratchet interface 43, 121.

The user torque required to rotate the dose selector 80 is a sum of the torque required to wind up the torsion spring 90, and the torque required to overhaul the ratchet interface 43, 121. The clutch spring 130 is designed to provide an axial force to the ratchet interface 43, 121 and to bias the clutch plate 120 onto the drive sleeve 40. This axial load acts to maintain the ratchet teeth engagement of the clutch plate 120 and drive sleeve 40. The torque required to overhaul the ratchet 43, 121 in the dose set direction is a function of the axial load applied by the clutch spring 130, the clockwise ramp angle of the ratchet teeth 43, 121, the friction coefficient between the mating surfaces and the mean radius of the ratchet interface 43, 121.

As the user rotates the dose selector 80 sufficiently to increment the mechanism by one increment, the number sleeve 60 rotates relative to the drive sleeve 40 by one ratchet tooth. At this point the ratchet teeth 43, 121 re-engage into the next detented position. An audible click is generated by the ratchet re-engagement, and tactile feedback is given by the change in torque input required.

Relative rotation of the number sleeve 60 and the drive sleeve 40 is allowed as splines 42, 61 are disengaged during dose setting. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface 43, 121 between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface 43, 121 between the number sleeve 60 and drive sleeve 40 is repeated for each dose increment. Additional energy is stored within the torsion spring 90 for each dose increment and audible and tactile feedback is provided for each increment dialled by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment 65 on the maximum dose abutment 112 of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment 51 with stop face 46 of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface 43, 121 between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e., from number sleeve 60, gauge element 110 and torsion spring 90. Splines 74 on the button 70 engage with splines 15 on the housing 10, preventing rotation of the button 70 (and hence the dose selector 80) during dispense. As the button 70 is stationary during dispense, it can be used in the dispense clicker mechanism as shown in FIG. 9a. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface 42, 61 between the drive sleeve 40 and number sleeve 60 as shown in FIGS. 7a (splines 42, 61 disengaged) and 7b (splines 42, 61 engaged), preventing relative rotation between the drive sleeve 40 and number sleeve 60 during dispense. The splined tooth interface 41, 14 between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment 64, 113 stops the mechanism.

The bearing 140 is axially clipped to the piston rod 30, but free to rotate. Since the bearing 140 is in direct contact with the bung 101, it does not rotate as the piston rod 30 rotates and advances during dose dispense. As described above, the contact diameter between the bearing 140 and piston rod 30 is small to minimise the frictional losses at this interface. The design of the piston rod 30 and bearing 140 eliminates delicate clip features or large contact diameters present on previous concepts. This embodiment also allows the piston rod 30 to be assembled axially, from the proximal end and through the thread engagement to the housing 10, which simplifies assembly.

Tactile feedback during dose dispense is provided via the compliant cantilever clicker arm 123 integrated into the clutch plate 120. This arm 123 interfaces radially with ratchet features 75 on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features 75 engage with the clicker arm 123 to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines 14, 41 between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialling only.

Once the delivery of a dose is stopped, by the number sleeve 60 returning to the zero dose abutment, the user may release the button 70, which will re-engage the spline teeth

14, 41 between the drive sleeve 40 and housing 10. The mechanism is now returned to the 'at rest' condition.

It is possible to angle the spline teeth 14, 41 on either the drive sleeve 40 or housing 10 so that when the button 70 is released the re-engagement of the spline teeth 14, 41 fractionally 'backwinds' the drive sleeve 40 thereby removing the engagement of the number sleeve 60 to the zero dose stop abutment on the gauge element 110. This compensates for the effect of clearances in the mechanism (for example due to tolerances) which could otherwise lead to slight advancement of the piston rod 30 and medicament dispense when the device is dialled for the subsequent dose due to the number sleeve 60 zero dose stop not restraining the mechanism and instead the restraint returning to the splines between the drive sleeve 40 and housing 10.

At the end of dose dispensing, additional audible feedback is provided in the form of a 'click', distinct from the 'clicks' provided during dispense, to inform the user that the device has returned to its zero position via the interaction of the clicker arm 67 on the number sleeve 60 with the ramp 47 on the drive sleeve 40 and the cam 117 and the recess 118 on the gauge element 110. This embodiment allows feedback to only be created at the end of dose delivery and not created if the device is dialled back to, or away from, the zero position.

FIG. 11a shows the position of the click features when the device is in the 'at rest' condition, with zero units dialled and the button 70 not depressed. It can be seen that the cam feature 117 on the gauge element 110 does not contact the clicker arm 67 on the number sleeve 60 when the button 70 is in the 'at rest' condition, so during storage or dialling the clicker arm 67 is not deflected.

During dialling, the gauge element 110 translates in the proximal direction, so the cam 117 is no longer aligned axially with the clicker arm 67. At the start of dose delivery when the drive sleeve 40 translates in the distal direction, the ramp 47 on the drive sleeve 40 pushes the clicker arm 67 radially outwards. During dose delivery, the gauge element 110 translates back in the distal direction, and towards the end of dose delivery, the clicker arm 67 contacts the cam 117 on the gauge element 110. For small doses, the cam 117 and clicker arm 67 will be in contact at the start of the dose. FIGS. 11b to 12c show the component interactions. After dose delivery, the button 70 is released and the end of dose mechanism returns to its 'at rest' position.

In FIG. 11b a dose is dialled and approximately one full dial turn is applied to number sleeve 60. Gauge element 110 is axially translated away from zero unit position, so that cam 117 is no longer aligned axially with clicker arm 67. FIG. 11c shows the start of dispensing, when button 70 is depressed to initiate dose dispense and which causes the drive sleeve 70 to translate axially. Ramp 47 on the drive sleeve 40 pushes clicker arm 67 radially out and into radial alignment with cam 117 on the gauge element 110.

Figures 12A, 12B, 12C, 13, 14:
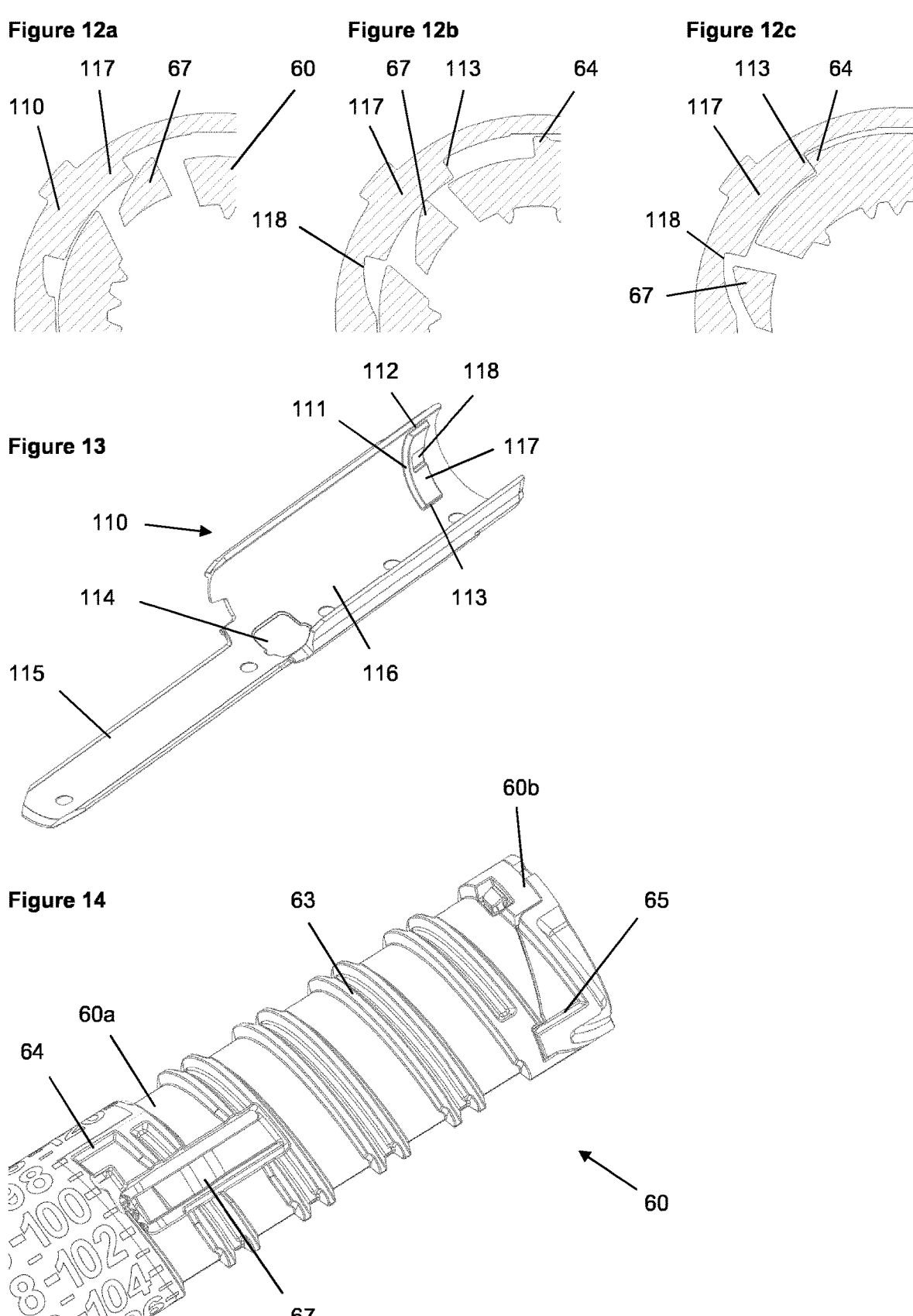
FIGS. 12a-c show in enlarged sectional views the sequence of generating a click at the end of dose dispensing of the device of FIG. 1.
FIG. 13 shows the gauge element of the device of FIG. 1.
FIG. 14 shows a portion of the number sleeve of the device of FIG. 1.

FIG. 12a shows the mechanism at the end of dose dispensing with approximately 4 units remaining. The gauge element 110 returns axially towards its zero unit position, so that cam 117 aligns axially with clicker arm 67. Rotation of number sleeve 60 causes clicker arm 67 to contact cam 117 such that clicker arm 67 is pushed radially inwards. With approximately 2 units remaining the number sleeve 60 rotates further and clicker arm 67 follows the profile of cam 117 (FIG. 12b). This radial deflection 'charges' clicker arm 67 storing elastic energy. In FIG. 12c dispensing is completed as the number sleeve 60 reaches its zero unit rotational position. The clicker arm 67 drops off the sharp edge of cam 117 into recess 118. Elastic energy is released causing clicker arm 67 to spring radially outwards to contact cam 117 and create a distinct 'click'.

In the principal embodiment of this disclosure, the lead screw 30 advances by a fixed displacement for each revolution of the drive sleeve 40. In other embodiments, the rate of displacement may vary. For example, the lead screw 30 may advance a large displacement per revolution to dispense a first amount of medicament from the cartridge 100 and then a smaller displacement per revolution to dispense the rest of the cartridge 100. This is advantageous, as it can compensate for the fact that the first dose dispensed from the cartridge 100 often has a lower volume than other doses, for a given displacement of the mechanism.

FIG. 22 shows three embodiments with the threads 16 of the housing 10 and the threads 31 of the lead screw 30 projected around the circumference. Arrow R indicates the direction of revolution of the lead screw 30 with respect to housing 10 for all three views.

View (a) shows the principal embodiment, where the pitch is equal on the housing 10 and lead screw 30, so the lead screw 30 advances a fixed amount for every revolution of the drive sleeve 40. In view (b), the first turn of thread 31 on the lead screw 30 has a large pitch, and the other turns have a small pitch. During the first revolution, the lead screw 30 displacement depends on the large pitch of the first turn of thread 31 on the lead screw 30, so it displaces a large amount per revolution. For subsequent revolutions the lead screw 30 displacement depends on the smaller pitch of the lead screw thread 31, so it displaces a smaller amount. In view (c), the housing 10 thread 16 has a larger pitch than the lead screw 30. During the first revolution, the lead screw 30 displacement depends on the pitch of the housing thread 16, so it displaces a large amount per revolution. For subsequent revolutions the lead screw 30 displacement depends on the pitch of the lead screw thread 31, so it displaces a smaller amount.

In one embodiment, the drug delivery device comprises a dose setting mechanism for setting a minimum dose size. Such a dose setting mechanism should ensure that the user cannot dispense less medicament than required.

As already described above, the drug delivery device comprises a number sleeve 60 which rotates in one direction, which is the dose setting direction, during dose setting. The number sleeve 60 rotates in the reverse direction during dispensing or correction of the set dose. The gauge element 110 engages the thread 63 on the number sleeve 60, resulting in an axial movement in the dose setting direction during setting and in the reverse direction during dispensing or correction.

Figure 23:
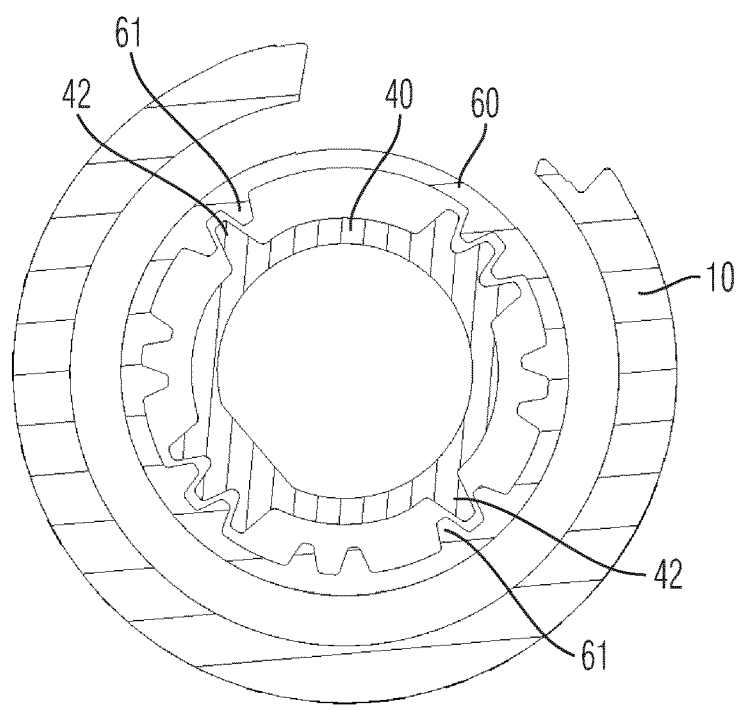
FIG. 23 shows a cross-section through the injection device only illustrating the housing, the driver and the dose indicator.

In FIG. 23 the spline engagement between the driver 40 and the dose indicator 60 is illustrated in greater detail. The driver 40 comprises radially outwardly extending lines 42 in the form of protrusions to engage with correspondingly shaped splines 61 protruding from an inside surface of the hollow shaped dose indicator 60 or number sleeve.

In FIGS. 24-28 one example of the injection device 1 is illustrated wherein the driver 40 forms a counterpart member 240 and wherein the dose indicator 60 forms a rotatable member 260 in the sense of the appended claims. As described above the injection device 1 is switchable between a dose setting mode, in which one of the rotatable member 260 and the counterpart member 240 is located in a proximal dose setting position s and a dose expelling mode in which the respective component, e.g., the rotatable member 260 or the counterpart member 240 is displaced in longitudinal direction I in to an expelling position e. In the examples of FIGS. 24-28 the rotatable member 260 forms the dose indicator 60. The rotatable member 260 is equivalent to the dose indicator 60 as described above. It may be substantially identical to the dose indicator 60 besides a second mechanical code 262 as will be described below in greater detail. The counterpart member 240 is equivalent to the driver 40 as described above. The counterpart member 240 may be substantially identically-shaped to the driver 40 besides a second mechanical code. The counterpart member 240 comprises a first mechanical code 242 that differs from the geometry of the driver 40 as described above in connection with FIGS. 1-23. The rotatable member 260 comprises or forms the number sleeve 60 that is threadedly engaged with the housing 10 as described above. The rotatable member 260 is axially fixed to the housing 10.

Figure 24:
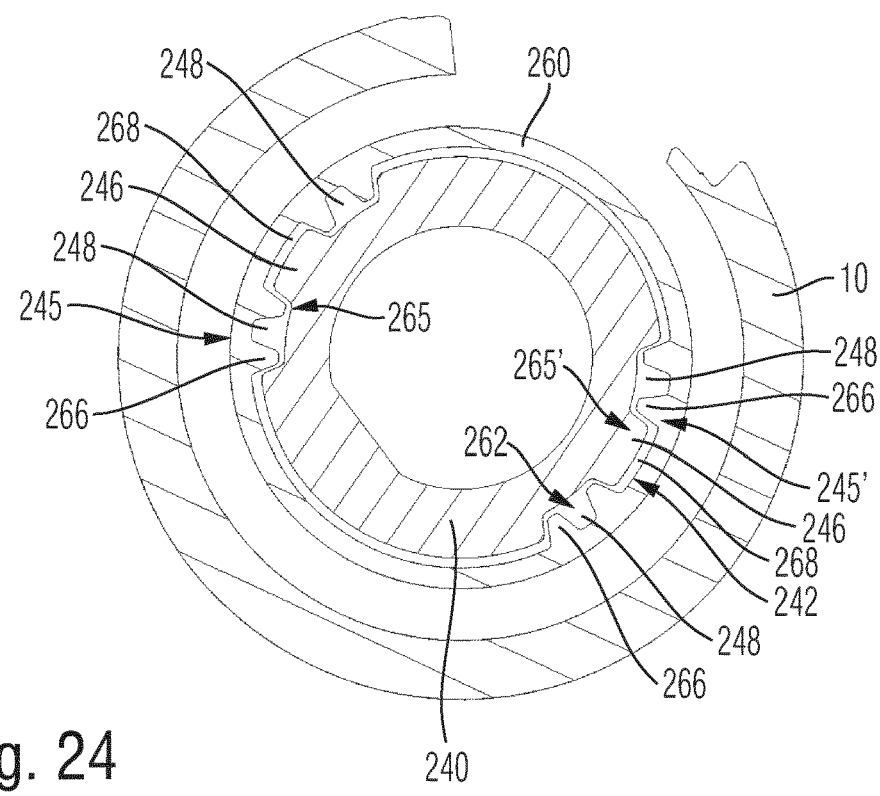
FIG. 24 shows a cross-section through the injection device wherein the driver forms a counterpart member and wherein the dose indicator forms a rotatable member.
Figure 25:
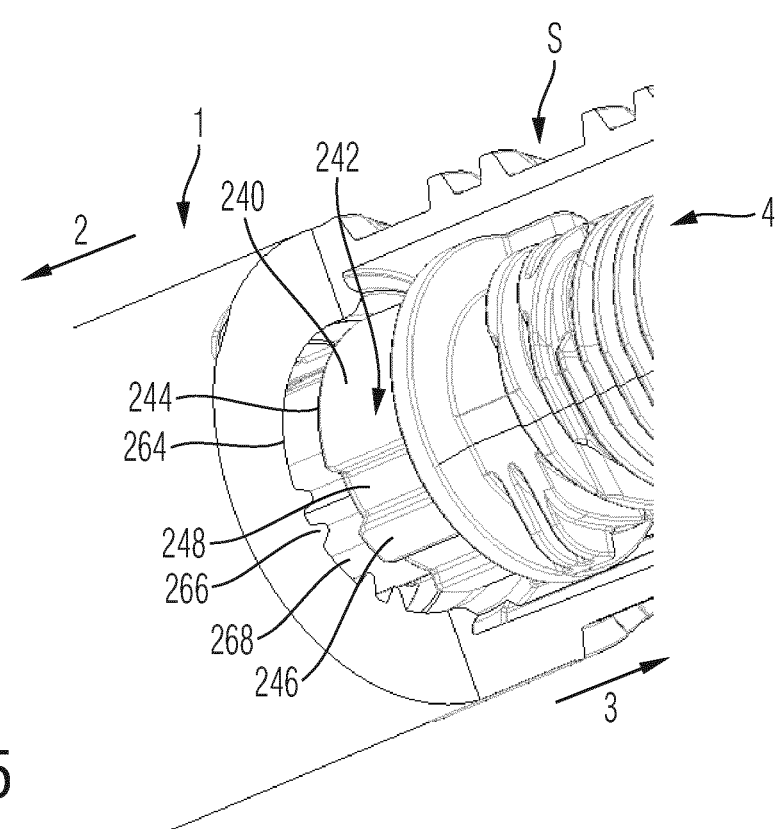
FIG. 25 is illustrative of the rotatable member and the counterpart member of FIG. 24 when first and second mechanical codes are aligned and when the injection device is in the dose setting mode.
Figure 26:
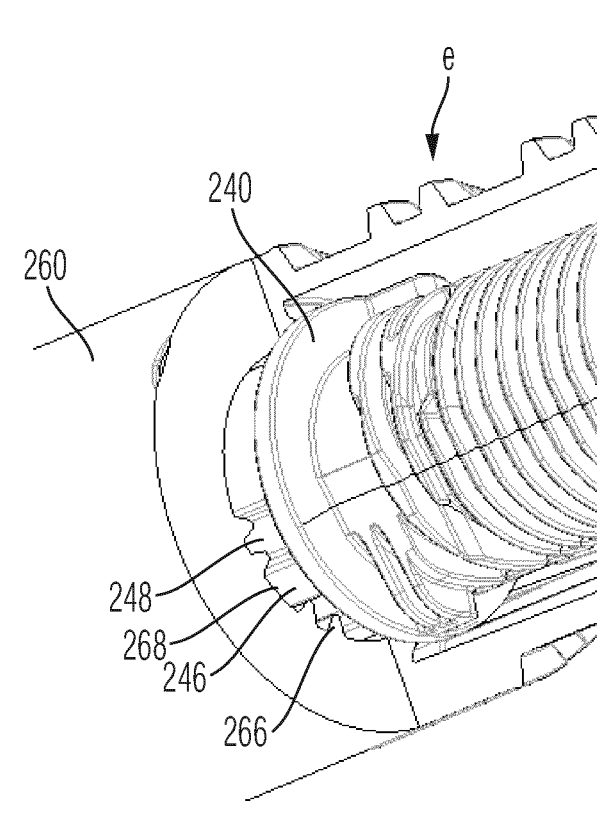
FIG. 26 shows the configuration according to FIG. 25 when the device is in the expelling mode.
Figure 27:
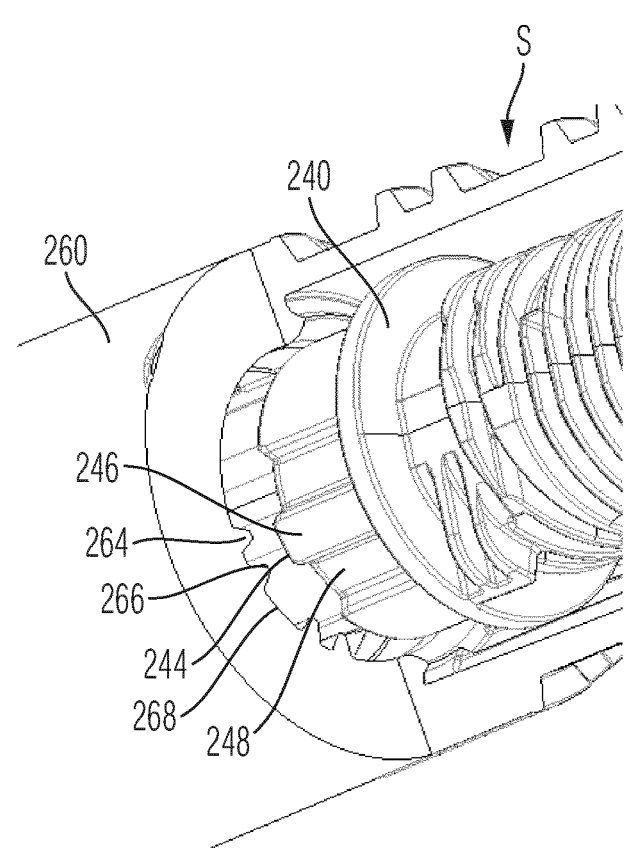
FIG. 27 shows a configuration similar to FIG. 25, wherein the first and the second codes are out of alignment.
Figure 28:
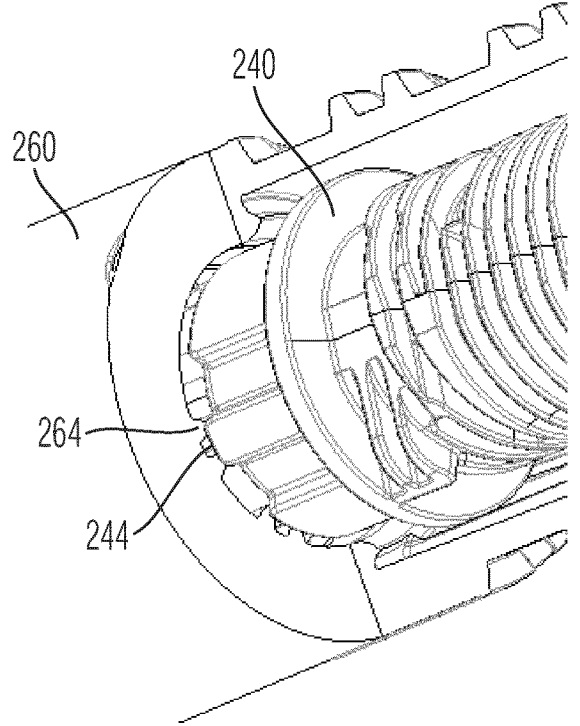
FIG. 28 shows the configuration of FIG. 27, wherein first and second mechanical codes prevent a switching of the injection device into the dose expelling mode.

In the example of FIGS. 24-28 the driver 40 is longitudinally displaceable between the dose setting position s as illustrated in FIGS. 25 and 27 and a dose expelling position e as illustrated in FIG. 26. A radially outwardly protruding portion may engage with a circumferential or annular groove on an inside of the sidewall of the housing 10 as illustrated in FIGS. 4a and 4b.

As illustrated in FIGS. 24-28 the rotatable member 260 comprises a second mechanical code 262. The counterpart member 240 comprises a first mechanical code 242. As illustrated in FIG. 24, each one of the first mechanical code 242 and the second mechanical code 262 comprises a first code feature 245, 265. The first code feature 245 of the first mechanical code 242 comprises at least one of a protrusion 246 and a recess 248. In the example as illustrated in FIG. 24, the first code feature 245 of the first mechanical code 242 comprises both, a radial protrusion 246 and a radial recess 248.

The first code feature 265 of the second mechanical code 262 comprises also at least one of a protrusion 266 and a recess 268. In the example as illustrated in FIG. 24, the first code feature 265 of the second mechanical code 262 comprises both, a radial protrusion 266 and a radial recess 268. Recesses 248, 268 and protrusions 246, 266 are complementary-shaped. The protrusion or the protrusions of one of the counterpart member 240 and the rotatable member 260 match with a recess or with recesses 248, 268 of the other one of the counterpart member 240 and the rotatable member 260. The rotatable member 260 and the counterpart member 240 are arrangeable in a nested or radially overlapping configuration. As illustrated in FIGS. 24-28 the rotatable member 260 comprises at least a hollow portion configured to slidably receive at least a portion of the counterpart member 240. As illustrated in FIGS. 25-28 the counterpart member 240 may be entirely located inside the hollow sleeve-shaped portion of the counterpart member 260.

With other examples currently not illustrated the counterpart member 240 may comprise a hollow portion configured to slidably receive at least a portion of the rotatable member 240 therein.

In the illustrated example the rotatable member 260 comprises at least a first code feature 265 on an inside of the hollow portion of the sidewall of the rotatable member 260. Correspondingly, the counterpart member 240 comprises the first code feature 245 on an outside surface of a sidewall.

As illustrated further in FIG. 24 the first mechanical code 242 comprises a first code feature 245 and a second code feature 245'. Also the second mechanical code 262 comprises a first code feature 265 and a second code feature 265'. The first and the second code features 245, 245' of the counterpart member 240 are arranged at a predefined angular distance from each other on the outer circumference or on an outside surface of the counterpart member 240. Correspondingly, the first and second code features 265, 265' of the second mechanical code 262 are located and arranged at a predefined distance from each other along the inner circumference of the rotatable member 260. As illustrated in FIG. 24, the angular or circumferential distance between the first and the second code features 245, 245' of the first mechanical code 242 equals the angular or circumferential distance between the first code feature 265 and the second code feature 265' of the second mechanical code 262.

In a further example the first and the second code features 245, 245' of the first mechanical code 242 may be arranged equidistantly or equiangularly along the outer circumference of the counterpart member 240. Likewise, the first code feature 265 and the second code feature 265' of the second mechanical code 262 may be equidistantly or equiangularly arranged on the inner circumference of the rotatable member 260.

As illustrated further in FIGS. 25 and 27 the protrusions 246 of the first mechanical code 242 comprise a radially outwardly protruding and longitudinally extending rib on the outer circumference of the counterpart member 240. The rib or protrusion 246 is formed by an adjacently located recess 248 that extends radially inwardly and forms an elongated groove in longitudinal direction on the outer circumference of the counterpart member 240.

Corresponding to the shape of the first mechanical code 242 the second mechanical code 262 on an inside surface of the rotatable member 260 comprises a radial recess 268 configured to receive the radial protrusion 246. The radial recess 268 may comprise an elongated groove on the inside surface of the rotatable member 260. The recess 268 is circumferentially confined by at least one protrusion 266 that is configured to engage with the recess 248 of the counterpart member 240.

The circumferential extension of the mutually corresponding protrusions 246, 266 and recesses 248, 268 are substantially equal so that a protrusion 246, 266 almost entirely fills the hollow space formed by a corresponding recess 248, 268.

In the example as illustrated in FIG. 24, the first code feature 245 and the second code feature 245' of the first mechanical code 248 are symmetric with regard to the center of the tubular-shaped counterpart member 240. The first code feature 265 and the second code feature 265' of the second mechanical code 262 are also symmetric with regard to the center of the sleeve or hollow-shaped rotatable member 260. Hence, the first and the second mechanical codes 242, 262 are invariant with regard to a rotation of 180° with regard to the principal or longitudinal axis I.

As described above, the rotatable member 260 is rotatable in a dose incrementing direction during setting of a dose. During dose setting and due to the ratchet engagement of the clutch plate 120 with the counterpart member 240 at the proximal end of the counterpart member 240 as described above in connection with the driver 40 actually represented by the counterpart member 240, the rotatable member 260 is rotatable into one of numerous discrete rotational states. The discrete rotational states are governed and determined by the step size of the ratchet engagement between the clutch plate 120 and the counterpart member 240. In one example and during a full revolution of the rotatable member 260, it may rest in one of 24 discrete rotational states relative to the housing 10.

As the injection device 1 is in the dose setting mode s the rotatable member 260 is rotatable as described above for setting of a dose. During setting of a dose, the first and second mechanical codes 242, 262 are axially offset. They are axially separated and out of engagement. Switching of the device into the dose expelling mode e and displacing the counterpart member 240 from the proximal dose setting position s into the distal dose expelling position e is only possible if the first mechanical code 242 is aligned longitudinally with the second mechanical code 262. Such an alignment is illustrated in FIG. 25. Here, the first and second code features 265, 265' of the second mechanical code 262 of the rotatable member 260 are located at the same angular position compared to the first and second code features 245, 245' of the first mechanical code 242 of the counterpart member 240.

In this particular predefined rotational state of the rotatable member 260 the counterpart member 240 can be displaced in axial direction, e.g., in distal direction 2 so that the first and the second mechanical codes 245, 245' of the counterpart member 240 engage and overlap with the first and second code features 265, 265' of the rotatable member 260. Due to the symmetric geometry and the equidistant arrangement of first and second code features 245, 245' and 265, 265' there are currently provided two allowable or predefined rotational states per revolution of the rotatable member 260 at which the injection device 1 can be switched from the dose setting mode into the dose expelling mode.

In the presently illustrated example there will be two distinct rotational states of the counterpart member 260 per full revolution at which a dose dispelling procedure can be triggered. In all other rotational states of the rotatable member 260 the mismatch of the first and the second mechanical codes 244, 262 and/or a rotational state of the second mechanical code 262 out of alignment with regard to the first mechanical code 242 prevents a distally directed displacement of the counterpart member 240 into the dose expelling position e. This is illustrated by a comparison of FIGS. 27 and 28.

In FIG. 27, the first mechanical code 242 is out of alignment with regard to the second mechanical code 262. As a consequence and if a user attempts to displace the counterpart member 240 into the expelling position e the alignment mismatch of the first and the second mechanical codes 242, 262 leads to a configuration wherein an abutment face 264 of the rotatable member 260 abuts with an abutment face 244 of the counterpart member 240. The abutment 264 comprises an abutment face pointing in the proximal direction. The abutment 244 or abutment face points in the distal direction. The abutment 264 may be located at a longitudinal end of the rotatable member 260 facing towards the counterpart member 240. The abutment 244 of the counterpart member 240 is located at a longitudinal end of one of the protrusions 246 facing towards the rotatable member 260.

In detail, the abutment 264 or abutment face may be located at a proximal end of a protrusion 266 and the abutment 244 or abutment face is typically located at a distal end of a protrusion 246. In case of a rotational alignment mismatch between the first mechanical code 242 and the second mechanical code 262 the counterpart member 240 cannot be displaced in longitudinal direction so that first and second mechanical codes 242, 262 mutually engage in a torque-proof way. Any further distally directed displacement of the counterpart member 240 and hence of the button or trigger 70 is effectively blocked and the dose dispensing or dose expelling procedure cannot be triggered.

Another example of a combination of a rotatable member 360 and a counterpart member 340 is illustrated in FIGS. 29-32. The expelling mechanism 4 and the dose setting mechanism 5 of this injection device is somewhat identical to the expelling mechanism 4 and the dose setting mechanism 5 as described above in connection to FIGS. 1-23. Here, the rotatable member 360 is substantially equivalent or identical to the button 70 as described above. The counterpart member 340 is substantially equivalent or identical to the housing 10 as described above. For implementing the example of FIGS. 29-32 only minor modifications to the button 70 and/or to the housing 10 are required in order to transform the button 70 into the rotatable member 360 and in order to transform the housing 10 into the counterpart member 340 as will be described below. Only minor modifications to the housing 10 and/or to the button 70 are required.

Figure 29:
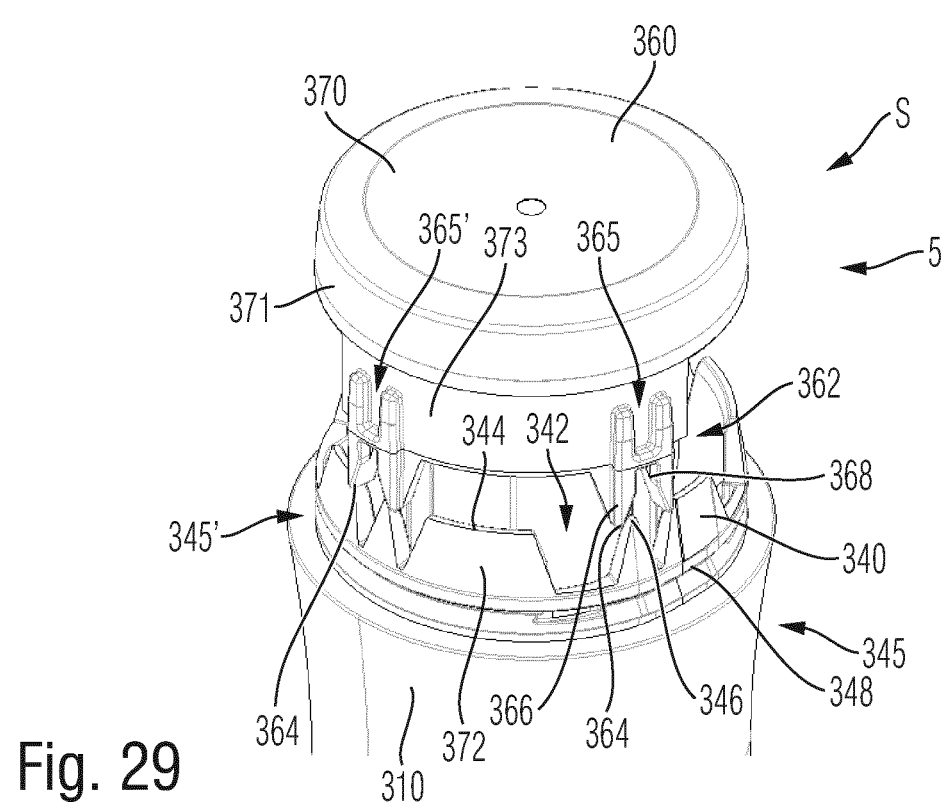
FIG. 29 is a perspective view of another example of the rotatable member and a counterpart member with first and second mechanical codes in alignment.
Figure 30:
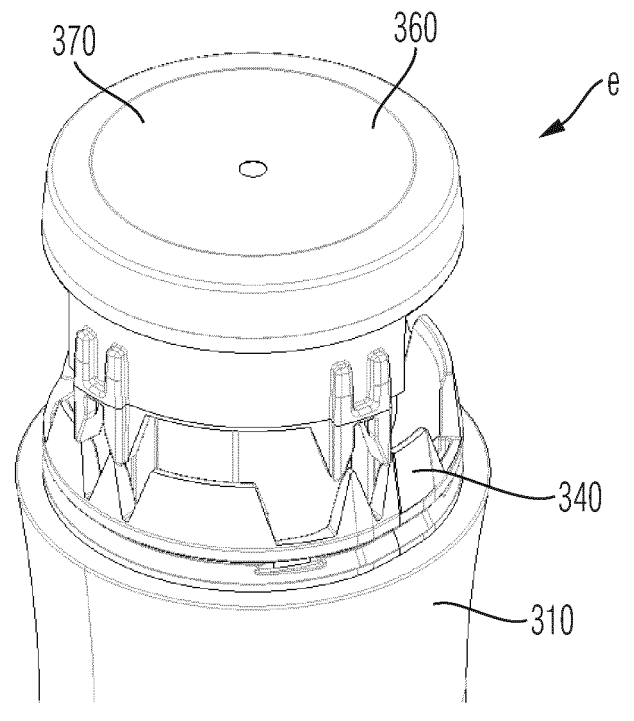
FIG. 30 is a further representation of the configuration of FIG. 29 wherein the injection device has been switched into the dose expelling mode.
Figure 31:
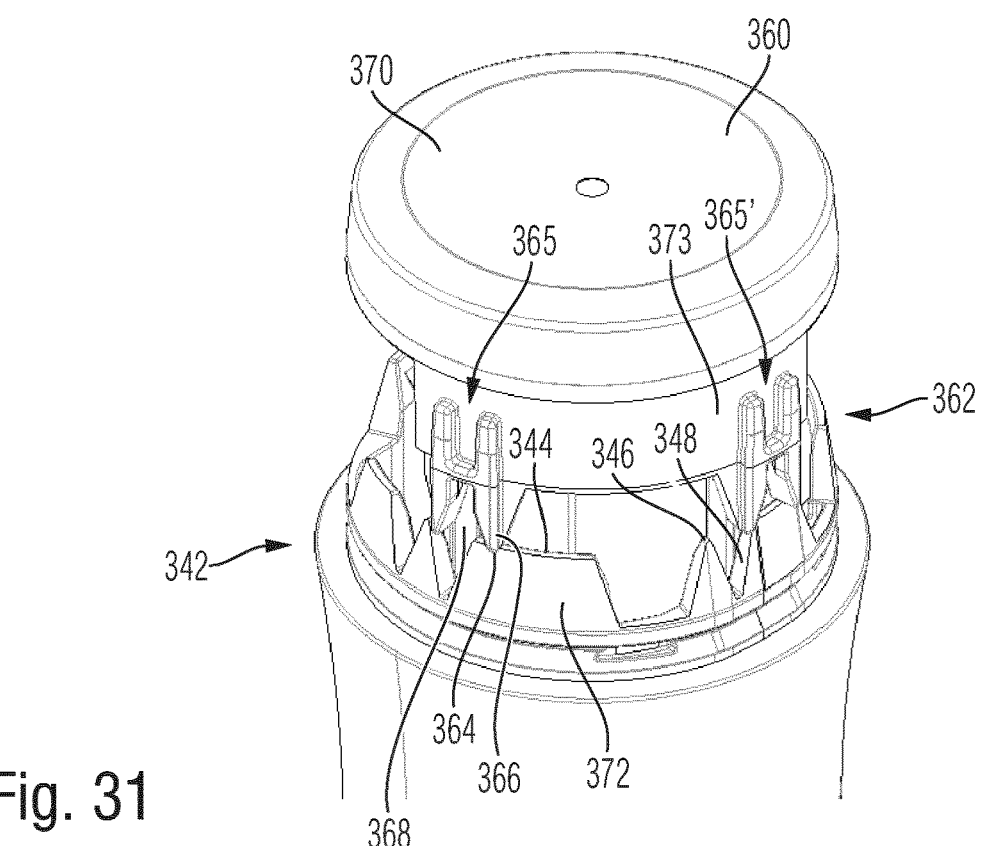
FIG. 31 shows the rotatable member and the counterpart member with first and second mechanical codes out of alignment.

As illustrated in FIG. 29 the rotatable member 360 forms the button 70 of the injection device 1. The rotatable member 360 or the button 360 comprises a planar-shaped proximal end face 370 and an annular skirt 371 extending in distal direction 2 from the outer circumference of the end face 370. On the skirt 371 and hence at a distal end of the rotatable member 360 there is provided a second mechanical code 362 complementary-shaped to a first mechanical code 342 at a proximal end of the counterpart member 340 or of the respective housing 310. For initiating or for controlling a dispensing action the rotatable member 360 or button 70 has to be displaced from a dose setting position s as illustrated in FIG. 29 into an expelling position e as illustrated in FIG. 30.

The proximal end face of the housing 310 is provided with the first mechanical code 342. The first mechanical code 342 comprises a first code feature 345 and a second code feature 345'. Each one of the first and second mechanical code features 345, 345' comprises a protrusion 346 and a recess 348. The second mechanical code 362 of the rotatable member 360 also comprises a first mechanical code feature 365 and a second mechanical code feature 365'. Each of the first and the second code features 365, 365' comprises at least one protrusion 366 and a recess 368. The protrusion 366 is shaped to engage with the recess 348. The recess 368 is shaped to engage with the protrusion 346. Contrary to the example as illustrated in FIGS. 24-28 with the example of FIGS. 29-32 the protrusions and recesses 346, 366, 348, 368 extend in longitudinal or axial direction.

Generally, the first mechanical code 342 replaces and modifies the splines 15 provided at the proximal end of the housing 10 as illustrated in FIG. 6. The first mechanical code 342 and/or the second mechanical code 362 may each comprise a toothed structure or a crown wheel structure.

It is further apparent in FIGS. 29-32, that these protrusions 366 at least slightly protrude radially outwardly from a skirt extension 373. This longitudinally elongated radial protrusion may engage with a correspondingly shaped longitudinal groove on an inside surface of the dose selector 80 or dial grip. In this way, the button 70 and the dial grip or dose selector 80 are permanently rotationally locked. The radially outwardly extending protrusion of the skirt extension 377 is also shown in FIG. 6.

Moreover, the protrusions 346, 366 and the recesses 348, 368 are tapered in the longitudinal direction. The protrusion 366 is tapered towards the distal direction 2. The protrusion 346 is tapered towards the proximal direction 3. In other words, the second mechanical code 362 comprises a toothed or geared structure and the first mechanical code 342 comprises a correspondingly-shaped toothed or geared structure. Circumferentially offset from the first and second code features 345, 345', 365, 365' there is provided an abutment face 344 that is, e.g., provided on a proximally raised rib 372. In this way and in an annular position of the rotatable member 360, in which the second mechanical code 362 is out of alignment with regard to the first mechanical code 342 a distally directed displacement of the rotatable member 360 relative to the housing 310 or relative to the counterpart member 340 is blocked by an axial abutment of one of the protrusions 366 with the abutment face 344 of the counterpart member 340.

Figure 32:
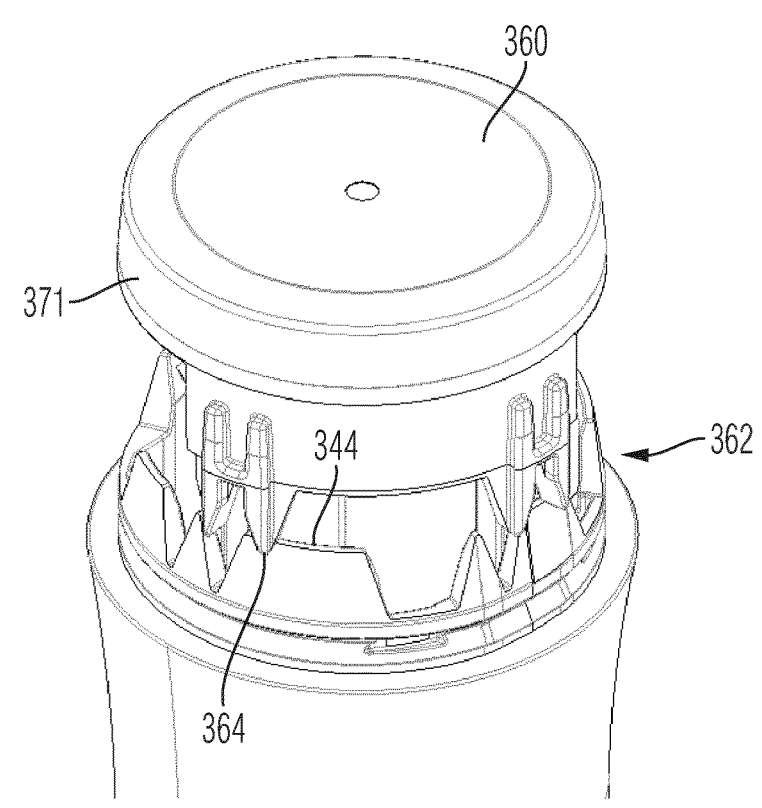
FIG. 32 shows the configuration of FIG. 31, wherein switching of the injection device into the expelling mode is impeded or blocked by the first and the second mechanical codes.

This situation is schematically illustrated in FIG. 32. Here, the distal end of a protrusion 366 of the rotatable member 360 equally serves and provides an abutment structure or an abutment face 364. If improperly aligned or in case of an alignment mismatch of the first and the second mechanical codes 342, 362 a depression of the rotatable member 360 towards the dose expelling position e is effectively blocked.

Only in a rotational state of the rotatable member 360, in which the second mechanical code 362 is longitudinally aligned with the first mechanical code 342 a distally directed advancing motion of the counterpart member 360 is allowed and supported. Then, and if correctly aligned the protrusions and recesses 366, 368 of the second mechanical code 362 engage with the correspondingly-shaped protrusions and recesses 346, 348 of the second mechanical code 342. The protrusions 366 may axially slide into the recesses 348. The protrusions 346 may slide into the recesses 368. As a consequence, the rotatable member 360 can be advanced and displaced in the distal direction and into the dose expelling position e in order to switch the injection device 1 from the dose setting mode into the dose dispensing mode as described above in connection with FIGS. 1-23.

With both of the examples as illustrated in FIGS. 24-28 and as illustrated in the FIGS. 29-32 the rotatable member 260, 360 and the counterpart member 240, 340 is rotationally locked and engaged in a torque-proof manner as the first and second mechanical codes 242, 342, 262, 362 are correctly aligned and as one of the counterpart member 240 and the rotatable member 360 arrives in the dose expelling position e. In this way, the first and second mechanical codes 242, 342, 262, 362 provides two functions. When in an alignment mismatch the first and second mechanical codes 242, 342, 262, 362 prevent and impede an injection procedure. If correctly aligned the first and the second mechanical codes 242, 342, 262, 362 not only enable and support a switching of the device into the dose expelling mode but also rotationally lock or rotationally connect the rotatable member 260, 360 to the counterpart member 240, 340.

In the dose expelling mode and with the example of FIGS. 24-28 the counterpart member 240 will be rotated by the rotatable member 260 in a dose decrementing direction under the action of the depleting torsion spring 90 thus transferring a driving torque to the lead screw 30 or piston rod. With the example of FIGS. 29-32 the torque-proof engagement between the rotatable member 360 and the counterpart member 340 prevents a rotational motion of the rotatable member 360 and hence of the trigger 70 relative to the housing 310 during a dose expelling procedure.

With both examples as illustrated in FIGS. 24-32 a number of permissible orientations can be individually set by adapting the geometry of the first and the second mechanical codes 242, 342, 262, 362. Basically, the above illustrated blocking of dose setting can be generally achieved when the first mechanical code 242, 342 and the second mechanical code 262, 362 comprise at least one code feature. However, having two or more code features along the circumference of the first and the second mechanical codes 242, 342, 262, 362 might be beneficial. In case of a blocking of the longitudinal movement of one of the rotatable member 360 and the counterpart member 240 the existence of numerous, e.g., two or more mutually engaging abutment faces 244, 344, 264, 364 is beneficial to distribute the respective longitudinally acting mechanical load between the counterpart member 240, 340 and the rotatable member 260, 360.

The permissible or predefined orientations of the rotatable member at which dose expelling is allowed should be equispaced around the circumference of the rotatable member. This ensures that the size of the predefined doses do not change after each dispensing or expelling procedure.

For the robustness of the mechanism as illustrated in FIGS. 24-32 it is beneficial that the number of protrusions of one of the first and second mechanical code 242, 342, 262, 362 is identical to the number of recesses of the other one of the first and second mechanical codes 242, 342, 262, 362. A torque to be transmitted across the interface of the counterpart member 240, 340 and the rotatable member 260, 360 may then be split between the number of available protrusions and recesses.

Having numerous mutually engaging code features along the circumference of the first and the second mechanical codes 242, 342, 262, 362 may be further beneficial to prevent tilting or to prevent a moving off center of at least one of the counterpart member 240 and the rotatable member 360 as these components are subject to a longitudinal displacement towards the expelling position e. Provided that the longitudinally displaceable components of the injection device are sufficiently prevented from tilting or from moving off center, some protrusions 246, 266, 346, 366 could be removed resulting in the same selectable dose regime. A reduced number of protrusions on the rotatable member 260 or of the dose indicator or number sleeve 60 may have the advantage, that only the counterpart member 240 or the driver 40 has to be modified compared to the implementation of FIGS. 1-23.

It may be further beneficial to add material to the counterpart member 240 and to remove material from the rotatable member 260 such that assembly of the counterpart member 240 and hence of the driver 40 to the rotatable member 260 and hence to the number sleeve or dose indicator 60 is not inhibited. Otherwise, the modifications to the dose indicator 60 and to the driver 40 do not affect the general handling and assembly process of the residual components of the injection device 1. Hence, one and the same fully automated or semi-automated assembly line can be used to produce a range of injection devices featuring different permissible dose sizes.

The same arguments and benefits also apply to the example of FIGS. 24-32. Also here, the number of permissible orientations of the rotatable member 360 can be set and adapted by the geometry of the mutually corresponding first and second mechanical codes 342, 362. Also here, permissible orientations should be equispaced around the circumference of the housing 310 to ensure that permitted doses do not change after each dispensing procedure. For the robustness of the mechanism it may be of advantage if for each protrusion 366 of the rotatable member 360 there is provided a matching cut out or recess 348 of the housing 310; and vice versa. In this way, a clutch torque or a holding force transferred from the housing 310 to the rotatable member 360 can be split between the number of teeth and protrusions. Moreover, also a stop force or an axial abutment force to block and to impede dispensing can be split between the number of teeth and the number of abutment faces 344, 364 for each non-permissible angular orientation of the rotatable member 360.

Provided that the rotatable member 360 is sufficiently prevented from tilting some of the protrusions 366 could be removed thus resulting in the same selectable dose regime. A reduced number of teeth or protrusions 366 may have the advantage that modifications of only the housing 310 are required compared to the illustration of the button 70 of FIG. 5a. In this way, the modifications required for implementing a prevention of unanticipated expelling procedures may not affect other features used during the assembly of the residual components of the injection device. Hence, with one and the same assembly line a wide range of injection devices can be produced featuring different permissible dose sizes. For this, only one of a housing 310 of a range of housings 310 featuring different mechanical codes 342 has to be selected.

The injection device 400 as illustrated in FIGS. 33-36 slightly differs from the injection device 1 as illustrated in the FIGS. 1-32. The injection device 400 is also of pen injector type. It comprises a distal end 402 configured for a releasable connection with a needle hub, which is presently not illustrated. It comprises a proximal end 403 with a trigger or a button 472. The basic functionality of the injection device 400 is comparable to the functionality of the injection device 1. The injection device 400 can be switched between a dose setting mode and a dose expelling mode by depressing the trigger 472 in distal direction. The injection device 400 comprises a cartridge holder 20 configured to accommodate a cartridge 100 filled with a liquid medicament 6.

In proximal direction the cartridge 100 is sealed by a bung 101. The cartridge holder 20 is connectable or is connected to a distal end of the body or housing 410 of the injection device 400. The injection device 400 comprises a dose expelling mechanism 4 and a dose setting mechanism 5 for setting and dispensing of a dose of the medicament 6. The injection device 400 comprises an elongated piston rod 430 threadedly engaged with a radially inwardly protruding flange 412 of the housing 410. The piston rod 430 is further in splined engagement with a driver 450 comprising a drive shaft or a drive sleeve and enclosing the piston rod 430. The driver 430 is snapped to a ratchet sleeve 480. It is axially fixed to the ratchet sleeve 480 and is rotationally locked to the ratchet sleeve 480. There may be a small amount of rotational play between the driver 450 and the ratchet sleeve 480. At the distal end of the piston rod 430 there is provided a rotatable bearing 432 acting as a pressure piece to exert distally directed pressure onto the bung 101.

The expelling mechanism is a wind up expelling mechanism. It comprises a torsion spring 490. One end of the torsion spring 490 is fixed and connected to the ratchet sleeve 480. An opposite end of the torsion spring 490 is connected to a stop member 541. The stop member 541 is steadfastly attached inside the housing 410. The injection device 400 further comprises a dose selector 482 rotatable relative to the housing and axially fixed to the housing 410. The button or trigger 472 is biased by a compression spring 474. It is depressible in the distal direction against the action of the spring 474. The button or trigger 472 is axially displaceable relative to the dose selector 482. It is configured to urge the driver 450 in the distal direction. There is a hooked connection between a stem 476 of the trigger 470 and a radially inwardly extending protrusion of the driver 450. When the button is depressed 472 in the distal direction it abuts axially with a proximal end of the driver 450 thus urging the driver 450 in the distal direction. Under the action of the spring 474 the button 472 is displaceable in the proximal direction and the snap connection to the driver 450 drags the driver 450 back into an initial dose setting position as for instance illustrated in FIGS. 33 and 34.

The housing 410 comprises a window 411 to visualize a portion of the outer circumference of the dose indicator 470. The outside of the dose indicator 470 is provided with consecutive numbers or other dose size indicating symbols that show up in the window 411 as the dose indicator 470 is subject to a rotation relative to the housing 410. The dose indicator 470 comprises a helical thread threadedly engaged with a correspondingly helical threaded structure on the inside surface of the sidewall of the housing 410. The dose indicator 470 is in splined engagement with the ratchet sleeve 480.

There is further provided a spline nut 434 and a locking nut 436. The spline nut 434 is in splined engagement with the lead screw 430. Hence, a rotation of the spline nut 434 leads to a rotation of the lead screw 430. The spline nut 434 may slide in an elongated groove on the lead screw 430 (not illustrated). The spline nut 434 is axially constrained inside the housing 410. The locking nut 436 is axially displaceable relative to the housing 410 between a dose setting position and a dose expelling position. In the dose setting position, hence in a proximal position the locking nut 436 is rotationally locked to the body via mutually corresponding splined sections. In the distal dose expelling position the locking nut 436 is rotationally locked to the spline nut 434 and is configured to transfer an angular momentum to the spline nut 434.

On an inside circumference of the locking nut 436 there is a toothed structure configured to engage with a ratchet feature provided on a distal sleeve portion 482 of the ratchet sleeve 480. For setting of a dose and as the ratchet sleeve 480 is rotated in a dose incrementing direction, the ratchet feature of the ratchet sleeve 480 generates an audible sound and defines a number of discrete rotational positions of the ratchet sleeve 480 relative to the housing 410. Each discrete angular position of the ratchet sleeve 480 corresponds and defines a particular size of a dose of the medicament 6. The ratchet sleeve 480, the driver 450 and the locking nut 436 are displaceable between the proximal dose setting position and the distal dose expelling position. In the dose setting position the dose selector 482 is rotationally locked to the driver 450. For this, a radially inwardly extending flange section of the dose selector 482 is in splined engagement with splines on the outside surface of a portion of the driver 450. Hence, a rotation of the dose selector 482 rotates the driver 450 and hence the ratchet sleeve 480. The ratchet feature of the ratchet sleeve 480 clicks over ratchet teeth inside the locking nut 436. The locking nut 436 is prevented from rotation by external ribs engaging teeth in the body. The ratchet feature or ratchet arm of the ratchet sleeve is strong enough to prevent stored energy in the torsion spring 490 from unwinding the selected dose.

For dispensing of a dose the user presses on the button or trigger 472 thus compressing the compression spring 474. The teeth on the driver 450 and the teeth or spline features of the dose selector 482 disengage and the dose selector 482 is hence rotationally disconnected from the driver 450. The distally directed displacement of the button or trigger 470 leads to a respective distally directed displacement of the driver 450 since the trigger 470 or button axially abuts a proximal end of the driver 450. As the driver 450 advances in distal direction also the locking nut 436 advances in distal direction together with the ratchet sleeve 480. The locking nut is hence disengaged from the teeth and the body and the locking nut 436 are free to rotate under the action of the depleting torsion spring 490. When in the dose expelling position the locking nut 436 is rotationally coupled or rotationally locked to the spline nut 434. Hence, a rotation of the locking nut 436 induced by the ratchet sleeve 480 driven under the action of the torsion spring 490 is unalteredly transferred to a rotation of the spline nut 434 thus rotating the lead screw 430, which due to the threaded engagement with the flange 412 advances in distal direction.

The injection device 400 may be also equipped with a last dose limiter as well as with a last dose limiter the functions of which are not further illustrated.

Figures 33, 34:
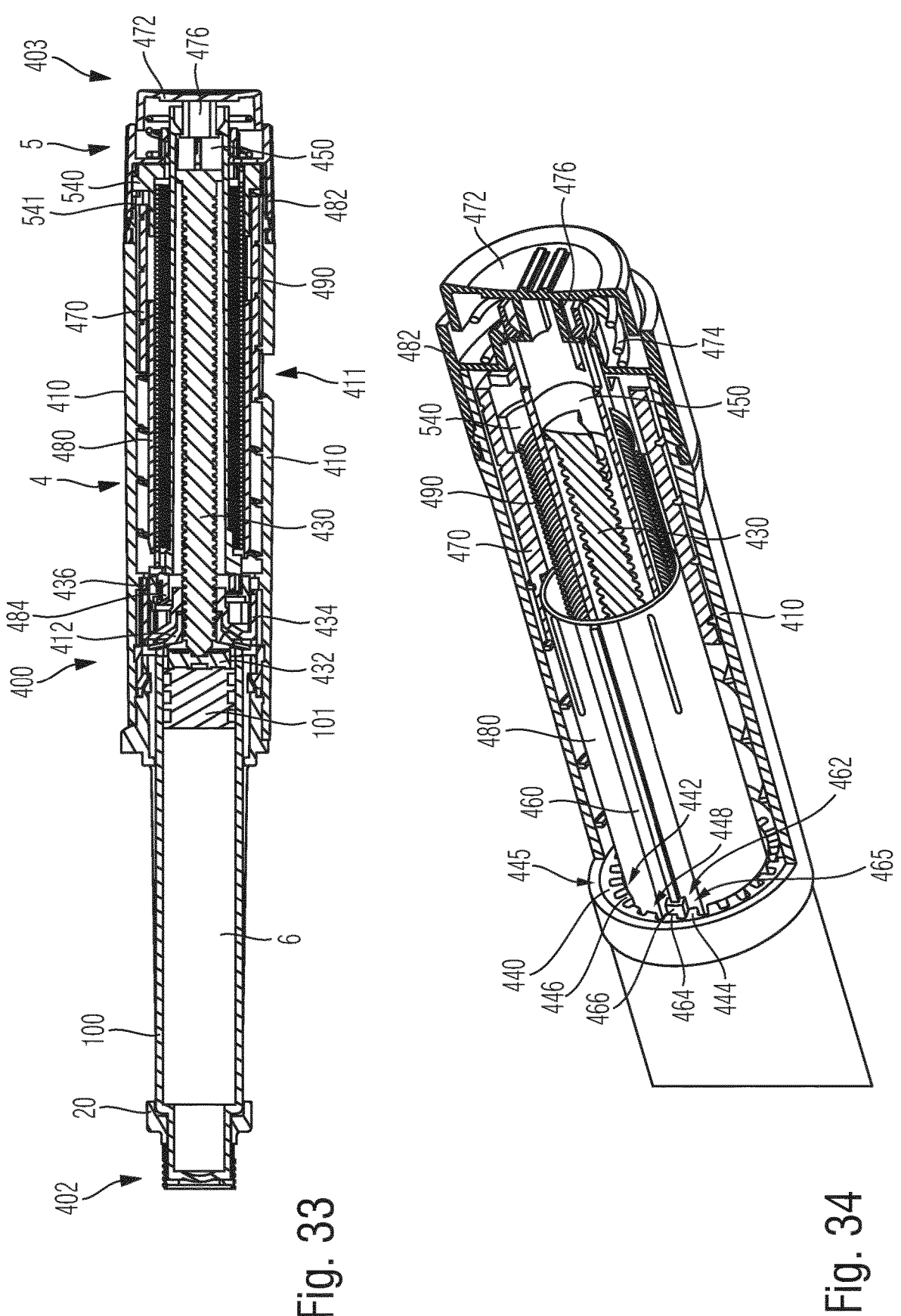
FIG. 33 is a longitudinal cross-section through a further example of an injection device.
FIG. 34 is a sectional and perspective view of a proximal portion of the injection device according to FIG. 33.

The ratchet sleeve 480 serves as a rotatable member 460 and the housing 410 provides a counterpart member 440 according to the terminology of the claims. As illustrated in FIG. 34 the rotatable member 460 comprises a second mechanical code 462 complementary-shaped to a first mechanical code 442 of the counterpart member 440. The first mechanical code 442 comprises a first mechanical code feature 445 and the second mechanical code 462 also comprises a first feature 465. The first code feature 465 comprises a radial protrusion 466 and the first code feature 445 comprises a radial recess 448. The code feature 445 further comprises numerous protrusions 446 separated by recesses that are smaller than the circumferential width of the protrusion 466.

Hence, the radial protrusion 466 of the rotatable member 460 must be longitudinally aligned with the recess 448 of the counterpart member 440. Only if the mutually corresponding first and second mechanical codes 442, 462 are aligned in longitudinal direction the rotatable member 460 can be displaced in distal direction 2 relative to the counterpart member 440 into the dose expelling position e. The first mechanical code 442 comprises an abutment face 444 facing in proximal direction and the second mechanical code 462 comprises an abutment face 466 facing in distal direction 2 on the radially outwardly extending protrusion 466. In case of a rotational alignment mismatch of the rotatable member 460 and the counterpart member 440 a distally directed displacement of the rotatable member 460 and hence of the ratchet sleeve 480 is blocked and impeded. Consequently, the injection device 400 cannot be switched from the dose setting mode into the dose expelling mode.

Even though not illustrated there may be provided numerous first and second code features on the outside circumference of the rotatable member 460 as well as on the inside circumference of the counterpart member 440. Depending on the shape and geometric configuration of the first and second mechanical codes 442, 462 various discrete and predefined allowable dose sizes can be defined. For this, there may be required only a modification of the first mechanical code 242 of the counterpart member.

Figure 35:
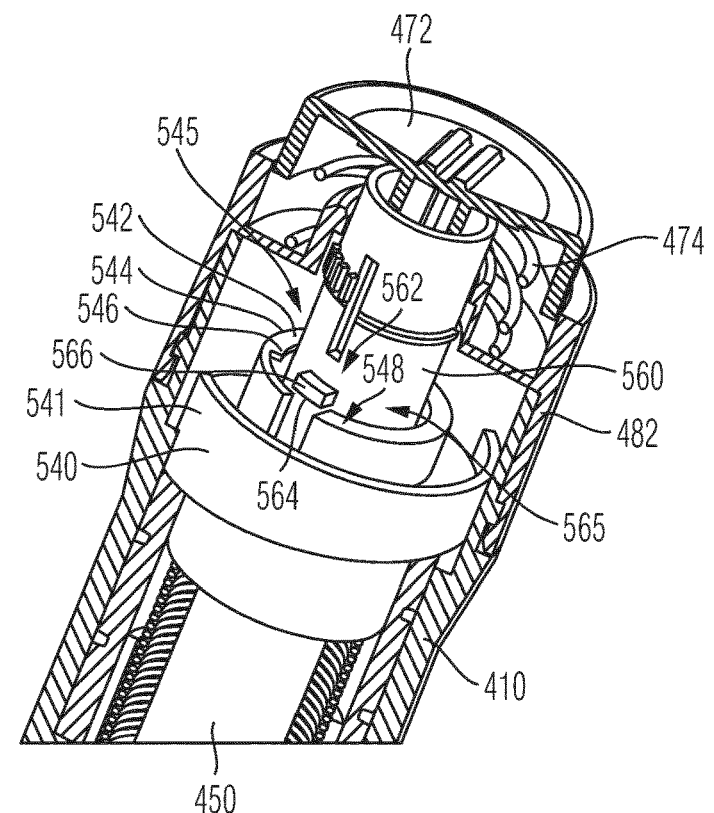
FIG. 35 is a further example of an injection device having a counterpart member and a rotatable member when in alignment.
Figure 36:
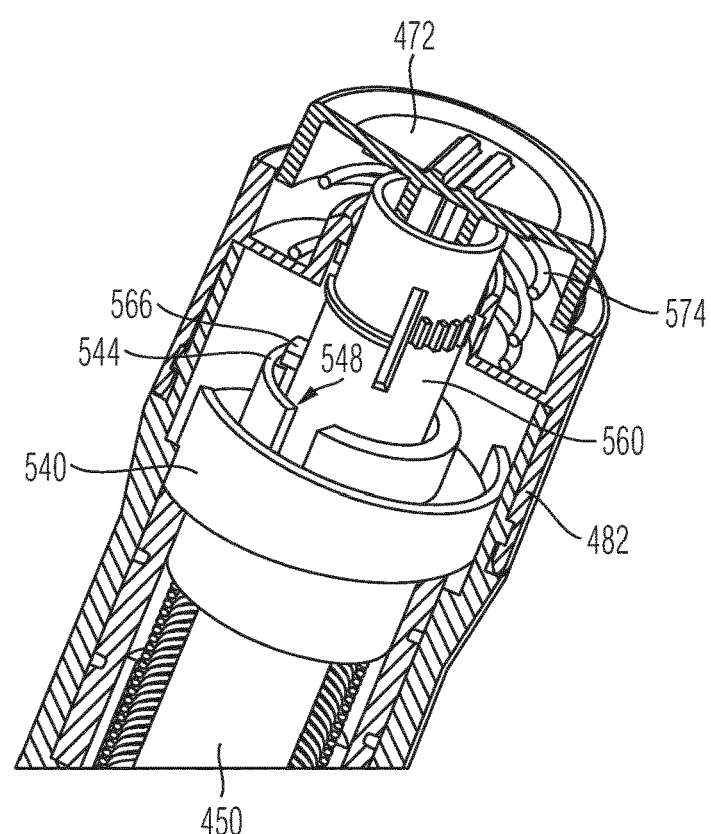
FIG. 36 shows the example of FIG. 35 when the first and the second mechanical code are out of alignment.

A further example of a rotatable member and of a counterpart member is illustrated in FIGS. 35 and 36. Here, the counterpart member 540 forms the stop member 541 or coincides with the stop member 541 steadfastly arranged inside the housing 410. The rotatable member 560 is formed by or constituted by the driver 450. The counterpart member 540 comprises a first mechanical code 542 complementary-shaped to a second mechanical code 562 of the rotatable member 560. The first mechanical code 542 comprises at least a first code feature 545. The first code feature 545 comprises at least one of a protrusion 546 and a recess 548. The protrusion 546 may comprise a radially inwardly extending flange on a sleeve-shaped section of the counterpart member 540. The recess 568 may comprise or may be formed as a recess or an interruption of the radially inwardly extending flange or protrusion 566.

The second mechanical code 562 comprises at least a first code feature 565. The first code feature 565 comprises at least one protrusion 566. The protrusion is a radially outwardly extending protrusion 566. The protrusion 566 is located at a predetermined angular position on an outside surface of the sleeve of the rotatable member 560, hence on the driver 450. In the dose setting position as illustrated the protrusion 566 and the protrusion 546 are separated by an axial distance or they may almost abut.

In the dose setting position the protrusion 566 of the rotatable member 560 is located proximally of the protrusion 546. In case of an alignment mismatch the protrusions 546, 566 are aligned in longitudinal direction. As the trigger 472 and hence the rotatable member 560 is subject to a distally directed displacement towards the expelling position a distally facing abutment 564 of the protrusion 566 abuts with a proximally facing abutment 544 of the protrusion 546. In this way, a further distally directed displacement of the rotatable member 560 is effectively blocked. It cannot reach the dose expelling position e and the injection device 400 cannot be switched into the dose expelling mode.

This configuration is illustrated in FIG. 36. As a consequence and due to the axial abutment of the trigger 472 and the rotatable member 560, also the trigger 472 cannot be depressed in distal direction 2. Here, the user experiences a rather direct mechanical and haptic feedback. Since there is only a minimal axial play between the trigger 472 and the driver 450 or rotatable member 560 a rather robust and immediate blocking that is substantially free of axial play can be provided to a user in case that the dose size actually dialled does not match with a predefined and required size of a dose.

In a different configuration as illustrated in FIG. 35, the dose selector 482 has been dialled to set a dose of predefined size. Here, the second mechanical code 562 is longitudinally aligned with the first mechanical code 542. The protrusion 566 is aligned with a correspondingly shaped recess 548 into which or through which the protrusion 566 is allowed to pass. Accordingly, the rotatable member 560 can be displaced into the dose expelling position e and the injection device 400 can be switched into the dose dispensing mode.

REFERENCE NUMERALS 1 injection device
2 distal direction
3 proximal direction
4 expelling mechanism
5 dose setting mechanism
6 medicament
10 housing
11a, b opening
12 flange-like inner wall
13 strip
14 teeth
15 spline
16 inner thread
20 cartridge holder
30 lead screw (piston rod)
31 outer thread
32 clip arm
33 concave contact surface
40 driver (axially movable drive sleeve)
41 teeth
42 spline 43 ratchet teeth
44 threaded section
45 spline
46 last dose stop
47 ramp
50 nut
51 last dose stop
52 spline
60 dose indicator (number sleeve)
60a number sleeve lower
60b number sleeve upper
61 spline
62 flange
63 outer thread
64, 65 end stop
66 spline
67 clicker arm
68 groove
69 anchor point
70 button
71 stem
72 flange
73, 74 spline
75 ratchet teeth
80 dose selector
90 torsion spring
91, 92 hook
93, 94 coil
100 cartridge
101 bung
110 gauge element
111 helical feature
112, 113 stop
114 aperture
115, 116 flange
117 cam
118 recess
120 clutch plate
121 ratchet teeth
122 protrusion
123 clicker arm
130 clutch spring
140 bearing
141 disc
142 stem
143 convex contact surface
144 recessed portion
240 counterpart member
242 mechanical code
244 abutment
245 code feature
246 protrusion
248 recess
260 rotatable member
262 mechanical code
264 abutment
265 code feature
266 protrusion
268 recess
310 housing
340 counterpart member
342 mechanical code
344 abutment
345 code feature
346 protrusion
348 recess
360 rotatable member 362 mechanical code
364 abutment
365 code feature
366 protrusion
368 recess
370 end face
371 skirt
372 rib
373 skirt extension
400 injection device
402 distal end
403 proximal end
410 housing
411 window
412 flange
430 piston rod
432 bearing
434 spline nut
436 locking nut
440 counterpart member
442 mechanical code
444 abutment
445 code feature
446 protrusion
448 recess
450 driver
460 rotatable member
462 mechanical code
464 abutment
465 code feature
466 protrusion
470 dose indicator
472 trigger
474 compression spring
476 stem
480 ratchet sleeve
482 dose selector
484 sleeve portion
490 torsion spring
540 counterpart member
541 stop member
542 mechanical code
544 abutment
545 code feature
546 protrusion
548 recess
560 rotatable member
562 mechanical code
564 abutment
565 code feature
566 protrusion

The invention claimed is:

1. An injection device for expelling a number of doses of a medicament, the injection device comprising:

an elongated housing extending along a longitudinal axis and configured to accommodate a cartridge, the cartridge containing the medicament and having a bung sealing a proximal end of the cartridge;

an expelling mechanism comprising a trigger and a piston rod, wherein when induced by the trigger the piston rod is configured to urge against the bung along the longitudinal axis in a distal direction relative to the housing; and a dose setting mechanism comprising a rotatable member and a counterpart member, wherein the counterpart member comprises a first mechanical pattern, and wherein the rotatable member comprises a second mechanical pattern complementary shaped to the first mechanical pattern, wherein the first mechanical pattern comprises at least one of a protrusion or a recess, and the second mechanical pattern comprises at least one of a complementary-shaped recess or protrusion, wherein for setting a dose the rotatable member is rotatable relative to the housing and relative to the counterpart member within a range of numerous rotational states, and wherein during setting of the dose, the rotatable member is constrained along the longitudinal axis relative to the housing or relative to the counterpart member, wherein for expelling the dose, one of the rotatable member or the counterpart member is displaceable along the longitudinal axis into an expelling position relative to the other one of the rotatable member or the counterpart member only when the first mechanical pattern is aligned with the second mechanical pattern.

2. The injection device according to claim 1, wherein a longitudinal displacement of one of the rotatable member or the counterpart member into the expelling position is impeded as long as the first mechanical pattern is out of alignment with respect to the second mechanical pattern.

3. The injection device according to claim 1, further comprising a dispensing spring compressible along the longitudinal axis and engaged with one of the rotatable member or the counterpart member, and wherein the rotatable member or the counterpart member is displaceable along the longitudinal axis from a dose setting position into the expelling position against the dispensing spring.

4. The injection device according to claim 1, wherein each of the first mechanical pattern and the second mechanical pattern comprises at least a respective second pattern feature comprising at least one of a protrusion or a recess, and wherein the respective first pattern features and the respective second pattern features are arranged at a predefined angular distance from each other on a circumference of at least one of the counterpart member or the rotatable member.

5. The injection device according to claim 1, wherein at least one of the first mechanical pattern or the second mechanical pattern comprises at least two or more pattern features equidistantly or equiangularly arranged on a circumference of at least one of the counterpart member or the rotatable member.

6. The injection device according to claim 1, wherein the protrusion is a radial protrusion and wherein the recess is a radial recess.

7. The injection device according to claim 6, wherein the radial protrusion comprises an elongated rib extending along the longitudinal axis.

8. The injection device according to claim 6, wherein the radial recess comprises an elongated groove extending along the longitudinal axis.

9. The injection device according to claim 1, wherein the protrusion is an axial protrusion extending along the longitudinal axis, and wherein the recess is an axial recess extending along the longitudinal axis.

10. The injection device according to claim 9, wherein at least one of the axial protrusion or the axial recess comprises a tapered or toothed structure pointing in a longitudinal direction along the longitudinal axis.

11. The injection device according to claim 1, wherein the counterpart member and the rotatable member are rotationally connectable or rotationally lockable to each other through the first mechanical pattern and the second mechanical pattern.

12. The injection device according to claim 11, wherein the counterpart member and the rotatable member are rotationally locked when one of the rotatable member or the counterpart member reaches the expelling position.

13. The injection device according to claim 1, wherein the counterpart member is integrated into the housing or is fixed to the housing, wherein the rotatable member is formed by the trigger or is displaceable along the longitudinal axis relative to the housing by depressing the trigger in the distal direction.

14. The injection device according to claim 1, further comprising a dose indicator and a drive sleeve, wherein the dose indicator forms the rotatable member and is threadedly engaged with the housing, and wherein the drive sleeve forms the counterpart member and is displaceable along the longitudinal axis relative to the housing by depressing of the trigger in the distal direction.

15. The injection device according to claim 1, further comprising the cartridge containing the medicament and arranged inside the housing.

16. An injection device comprising:

an elongated housing extending along a longitudinal axis and configured to accommodate a cartridge, the cartridge containing a medicament; and a dose setting mechanism comprising a rotatable member and a counterpart member, wherein the counterpart member comprises a first mechanical pattern, and wherein the rotatable member comprises a second mechanical pattern complementary shaped to the first mechanical pattern, wherein the first mechanical pattern comprises at least one of a protrusion or a recess, and wherein the second mechanical pattern comprises at least one of a complementary-shaped recess or protrusion, wherein for setting a dose the rotatable member is rotatable relative to the housing and relative to the counterpart member within a range of numerous rotational states, and wherein during setting of the dose the rotatable member is constrained along the longitudinal axis relative to the housing or relative to the counterpart member, wherein for expelling the dose one of the rotatable member or the counterpart member is displaceable along the longitudinal axis into an expelling position relative to the other one of the rotatable member or the counterpart member when the first mechanical pattern is aligned with the second mechanical pattern.

17. The injection device according to claim 16, wherein a longitudinal displacement of one of the rotatable member or the counterpart member into the expelling position is impeded as long as the first mechanical pattern is out of alignment with respect to the second mechanical pattern.

18. The injection device according to claim 16, further comprising a dispensing spring compressible along the longitudinal axis and engaged with one of the rotatable member or the counterpart member, and wherein the rotatable member or the counterpart member is displaceable along the longitudinal axis from a dose setting position into the expelling position against the dispensing spring.

* * * * *